(12) United States Patent
Dhar et al.

(10) Patent No.: US 10,416,167 B2
(45) Date of Patent: Sep. 17, 2019

(54) NANOPARTICLES FOR MITOCHONDRIAL TRAFFICKING OF AGENTS

(71) Applicant: UNIVERSITY OF GEORGIA RESEARCH FOUNDATION, INC., Athens, GA (US)

(72) Inventors: Shanta Dhar, Miami, FL (US); Sean M. Marrache, Portland, OR (US)

(73) Assignee: University of Georgia Research Foundation, Inc., Athens, GA (US)

( * ) Notice: Subject to any disclaimer, the term of this patent is extended or adjusted under 35 U.S.C. 154(b) by 745 days.

(21) Appl. No.: 14/378,813

(22) PCT Filed: Feb. 15, 2013

(86) PCT No.: PCT/US2013/026299
§ 371 (c)(1),
(2) Date: Aug. 14, 2014

(87) PCT Pub. No.: WO2013/123298
PCT Pub. Date: Aug. 22, 2013

(65) Prior Publication Data
US 2016/0022825 A1 Jan. 28, 2016

Related U.S. Application Data

(60) Provisional application No. 61/600,088, filed on Feb. 17, 2012.

(51) Int. Cl.
| | |
|---|---|
| *G01N 33/58* | (2006.01) |
| *A61K 31/06* | (2006.01) |
| *A61K 31/12* | (2006.01) |
| *A61K 31/355* | (2006.01) |
| *A61K 31/416* | (2006.01) |
| *A61K 49/00* | (2006.01) |
| *A61K 47/60* | (2017.01) |
| *A61K 47/54* | (2017.01) |
| *A61K 47/69* | (2017.01) |
| *B82Y 5/00* | (2011.01) |
| *A61K 9/51* | (2006.01) |

(52) U.S. Cl.
CPC ............ *G01N 33/587* (2013.01); *A61K 31/06* (2013.01); *A61K 31/12* (2013.01); *A61K 31/355* (2013.01); *A61K 31/416* (2013.01); *A61K 47/548* (2017.08); *A61K 47/60* (2017.08); *A61K 47/6937* (2017.08); *A61K 49/0067* (2013.01); *A61K 49/0093* (2013.01); *G01N 33/588* (2013.01); *A61K 9/5153* (2013.01); *B82Y 5/00* (2013.01)

(58) Field of Classification Search
CPC ........ A61K 47/48084; A61K 47/48915; A61K 49/0067; A61K 9/5153; A61K 31/06; A61K 31/12; A61K 31/416; A61K 49/0093; A61K 47/48215; A61K 31/355; G01N 33/588; G01N 33/587; B82Y 5/00
See application file for complete search history.

(56) References Cited

U.S. PATENT DOCUMENTS

| | | | |
|---|---|---|---|
| 6,217,864 | B1 | 4/2001 | Coffino et al. |
| 6,753,154 | B1 | 6/2004 | Chen et al. |
| 6,835,718 | B2 | 12/2004 | Kosak |
| 7,329,638 | B2 | 2/2008 | Yang et al. |
| 7,393,924 | B2 | 7/2008 | Vitaliano et al. |
| 7,638,558 | B2 | 12/2009 | Breitenkamp et al. |
| 7,671,095 | B2 | 3/2010 | Colson et al. |
| 7,725,169 | B2 | 5/2010 | Boppart et al. |
| 7,728,036 | B2 | 6/2010 | Huang et al. |
| 7,858,843 | B2 | 12/2010 | Culbertson et al. |
| 7,931,902 | B2 | 4/2011 | De Sauvage et al. |
| 7,935,782 | B2 | 5/2011 | Harth et al. |
| 7,947,866 | B2 | 5/2011 | Sparks |
| 7,956,237 | B2 | 6/2011 | Montgomery et al. |
| 8,067,664 | B2 | 11/2011 | Huang |
| 8,128,908 | B2 | 3/2012 | Santra et al. |
| 8,178,527 | B2 | 5/2012 | Chen et al. |
| 8,207,396 | B2 | 6/2012 | Payne et al. |
| 8,221,480 | B2 | 7/2012 | Boyden et al. |
| 8,227,661 | B2 | 7/2012 | Edwards et al. |
| 8,256,233 | B2 | 9/2012 | Boyden et al. |
| 8,263,663 | B2 | 9/2012 | Sill et al. |
| 8,263,665 | B2 | 9/2012 | Sill et al. |
| 8,273,373 | B2 | 9/2012 | Alsberg et al. |

(Continued)

FOREIGN PATENT DOCUMENTS

| | | |
|---|---|---|
| EP | 1995321 A2 | 11/2008 |
| EP | 2002714 A1 | 12/2008 |

(Continued)

OTHER PUBLICATIONS

European Patent Application No. 13 74 9000.9, filed Sep. 5, 2014; Extended European Search Report and Search Opinion dated Sep. 21, 2015; 13 pages.

(Continued)

*Primary Examiner* — Robert S Cabral
(74) *Attorney, Agent, or Firm* — Mueting, Raasch & Gebhardt, P.A.

(57) ABSTRACT

Nanoparticles include a core, a hydrophilic layer around the core, and one or more mitochondrial targeting moieties, and may optionally include one or more contrast agents or one or more therapeutic agents. For effective mitochondrial targeting the nanoparticles have a diameter of about 200 nm or less or have a zeta potential of about 0 mV or more.

24 Claims, 13 Drawing Sheets

(56) References Cited

U.S. PATENT DOCUMENTS

| | | | |
|---|---|---|---|
| 8,282,967 B2 | 10/2012 | Schoenfisch et al. | |
| 8,297,959 B2 | 10/2012 | Larsen et al. | |
| 8,299,128 B2 | 10/2012 | Sill et al. | |
| 8,449,915 B1* | 5/2013 | Sung | A61K 49/1845 424/489 |
| 2001/0021703 A1 | 9/2001 | Kosak | |
| 2004/0038406 A1 | 2/2004 | Unger et al. | |
| 2005/0025820 A1 | 2/2005 | Kester et al. | |
| 2005/0042753 A1 | 2/2005 | Yang et al. | |
| 2005/0153913 A1 | 7/2005 | Kosak | |
| 2006/0040879 A1 | 2/2006 | Kosak | |
| 2006/0228299 A1 | 10/2006 | Thorpe et al. | |
| 2006/0240092 A1 | 10/2006 | Breitenkamp et al. | |
| 2006/0292099 A1 | 12/2006 | Milburn et al. | |
| 2007/0014833 A1 | 1/2007 | Milburn et al. | |
| 2007/0066552 A1 | 3/2007 | Clarke et al. | |
| 2007/0098713 A1 | 5/2007 | Unger et al. | |
| 2007/0134340 A1 | 6/2007 | Prasad et al. | |
| 2007/0141163 A1 | 6/2007 | Vitaliano et al. | |
| 2007/0258889 A1 | 11/2007 | Douglas et al. | |
| 2007/0269382 A1 | 11/2007 | Santra et al. | |
| 2007/0292353 A1* | 12/2007 | Levy | A61K 41/0071 424/9.34 |
| 2007/0292438 A1 | 12/2007 | Anderson et al. | |
| 2007/0296099 A1 | 12/2007 | Larsen et al. | |
| 2008/0051323 A1 | 2/2008 | Kosak | |
| 2008/0069857 A1 | 3/2008 | Yeo et al. | |
| 2008/0075718 A1 | 3/2008 | Colson et al. | |
| 2008/0124344 A1 | 5/2008 | Combs et al. | |
| 2008/0160034 A1 | 7/2008 | Brennan et al. | |
| 2008/0187487 A1 | 8/2008 | Larsen et al. | |
| 2008/0243049 A1 | 10/2008 | Hardy | |
| 2008/0294089 A1 | 11/2008 | Hardy | |
| 2008/0299177 A1 | 12/2008 | Hardy | |
| 2008/0299182 A1 | 12/2008 | Zhang et al. | |
| 2008/0305106 A1 | 12/2008 | Zhang et al. | |
| 2008/0311045 A1 | 12/2008 | Hardy | |
| 2008/0311107 A1 | 12/2008 | Bollinger et al. | |
| 2008/0312581 A1 | 12/2008 | Hardy | |
| 2008/0319375 A1 | 12/2008 | Hardy | |
| 2009/0018078 A1 | 1/2009 | Van Landingham, Jr. et al. | |
| 2009/0022806 A1 | 1/2009 | Mousa et al. | |
| 2009/0092582 A1 | 4/2009 | Bogin et al. | |
| 2009/0124534 A1 | 5/2009 | Reineke | |
| 2009/0142348 A1 | 6/2009 | De Sauvage et al. | |
| 2009/0148384 A1 | 6/2009 | Fischer et al. | |
| 2009/0155349 A1 | 6/2009 | Heller et al. | |
| 2009/0169521 A1 | 7/2009 | Levenberg et al. | |
| 2009/0196876 A1 | 8/2009 | De Sauvage et al. | |
| 2009/0214618 A1 | 8/2009 | Schoenfisch et al. | |
| 2009/0288176 A1 | 11/2009 | Bollinger et al. | |
| 2009/0293137 A1 | 11/2009 | Combs et al. | |
| 2009/0306225 A1 | 12/2009 | Lichter et al. | |
| 2009/0313707 A1 | 12/2009 | Combs et al. | |
| 2010/0015050 A1 | 1/2010 | Panyam et al. | |
| 2010/0015228 A1 | 1/2010 | Lichter et al. | |
| 2010/0015263 A1 | 1/2010 | Lichter et al. | |
| 2010/0016218 A1 | 1/2010 | Lichter et al. | |
| 2010/0021416 A1 | 1/2010 | Lichter et al. | |
| 2010/0022661 A1 | 1/2010 | Lichter et al. | |
| 2010/0028994 A1 | 2/2010 | Desimone et al. | |
| 2010/0031378 A1 | 2/2010 | Edwards et al. | |
| 2010/0035341 A1 | 2/2010 | Itskovitz-Eldor et al. | |
| 2010/0048736 A1 | 2/2010 | Liu et al. | |
| 2010/0068141 A1 | 3/2010 | Kaushal et al. | |
| 2010/0068806 A1 | 3/2010 | Lane et al. | |
| 2010/0076018 A1 | 3/2010 | Liu et al. | |
| 2010/0111837 A1 | 5/2010 | Boyden et al. | |
| 2010/0111846 A1 | 5/2010 | Boyden et al. | |
| 2010/0111847 A1 | 5/2010 | Boyden et al. | |
| 2010/0111848 A1 | 5/2010 | Boyden et al. | |
| 2010/0111849 A1 | 5/2010 | Boyden et al. | |
| 2010/0111850 A1 | 5/2010 | Boyden et al. | |
| 2010/0111854 A1 | 5/2010 | Boyden et al. | |
| 2010/0111855 A1 | 5/2010 | Boyden et al. | |
| 2010/0111938 A1 | 5/2010 | Boyden et al. | |
| 2010/0112067 A1 | 5/2010 | Boyden et al. | |
| 2010/0112068 A1 | 5/2010 | Boyden et al. | |
| 2010/0113614 A1 | 5/2010 | Boyden et al. | |
| 2010/0114348 A1 | 5/2010 | Boyden et al. | |
| 2010/0114547 A1 | 5/2010 | Boyden et al. | |
| 2010/0119557 A1 | 5/2010 | Boyden et al. | |
| 2010/0121466 A1 | 5/2010 | Boyden et al. | |
| 2010/0113615 A1 | 6/2010 | Mulfinger et al. | |
| 2010/0143243 A1 | 6/2010 | Boyden et al. | |
| 2010/0144641 A1 | 6/2010 | Popel et al. | |
| 2010/0152651 A1 | 6/2010 | Boyden et al. | |
| 2010/0152880 A1 | 6/2010 | Boyden et al. | |
| 2010/0159020 A1 | 6/2010 | Breitenkamp et al. | |
| 2010/0163576 A1 | 7/2010 | Boyden et al. | |
| 2010/0168900 A1 | 7/2010 | Boyden et al. | |
| 2010/0185174 A1 | 7/2010 | Boyden et al. | |
| 2010/0187728 A1 | 7/2010 | Boyden et al. | |
| 2010/0196280 A1 | 8/2010 | Fischer et al. | |
| 2010/0196481 A1 | 8/2010 | Pritchard et al. | |
| 2010/0215760 A1 | 8/2010 | Kundu et al. | |
| 2010/0233153 A1 | 9/2010 | Borromeo et al. | |
| 2010/0256232 A1 | 10/2010 | White et al. | |
| 2010/0260706 A1 | 10/2010 | Bogin et al. | |
| 2010/0273864 A1 | 10/2010 | Lichter et al. | |
| 2010/0331819 A1 | 12/2010 | Hossainy et al. | |
| 2011/0008304 A1 | 1/2011 | Troyer et al. | |
| 2011/0008443 A1 | 1/2011 | Alsberg et al. | |
| 2011/0034422 A1 | 1/2011 | Kannan et al. | |
| 2011/0028181 A1 | 2/2011 | Byun et al. | |
| 2011/0028395 A1 | 2/2011 | Popel et al. | |
| 2011/0028945 A1 | 2/2011 | Amodei et al. | |
| 2011/0038939 A1 | 2/2011 | Lvov et al. | |
| 2011/0052715 A1 | 3/2011 | Davis et al. | |
| 2011/0061114 A1 | 3/2011 | Edwards et al. | |
| 2011/0091534 A1 | 4/2011 | Breitenkamp et al. | |
| 2011/0092668 A1 | 4/2011 | Breitenkamp et al. | |
| 2011/0093960 A1 | 4/2011 | Edwards et al. | |
| 2011/0097330 A1 | 4/2011 | Horner et al. | |
| 2011/0130325 A1 | 6/2011 | Labhasetwar | |
| 2011/0142941 A1 | 6/2011 | Davis et al. | |
| 2011/0150765 A1 | 6/2011 | Boyden et al. | |
| 2011/0152305 A1 | 6/2011 | Colson et al. | |
| 2011/0172826 A1 | 7/2011 | Amodei et al. | |
| 2011/0173708 A1 | 7/2011 | Combs et al. | |
| 2011/0182883 A1 | 7/2011 | Combs et al. | |
| 2011/0191865 A1 | 8/2011 | Edwards et al. | |
| 2011/0200579 A1 | 8/2011 | Cunningham et al. | |
| 2011/0203013 A1 | 8/2011 | Peterson et al. | |
| 2011/0244048 A1 | 10/2011 | Amiji et al. | |
| 2011/0245207 A1* | 10/2011 | Skulachev | A61K 31/66 514/130 |
| 2011/0252485 A1 | 10/2011 | De Sauvage et al. | |
| 2011/0274620 A1 | 11/2011 | Harth et al. | |
| 2011/0274747 A1 | 11/2011 | Habener et al. | |
| 2012/0005766 A1 | 1/2012 | Bollinger et al. | |
| 2012/0015039 A1 | 1/2012 | Sexton et al. | |
| 2012/0021055 A1 | 1/2012 | Schoenfisch et al. | |
| 2012/0027681 A1 | 2/2012 | Jung et al. | |
| 2012/0030776 A1 | 2/2012 | Combs et al. | |
| 2012/0034169 A1 | 2/2012 | Schoenfisch et al. | |
| 2012/0045389 A1 | 2/2012 | Gassull Duro et al. | |
| 2012/0046346 A1 | 2/2012 | Rossi et al. | |
| 2012/0058505 A1 | 3/2012 | Helms et al. | |
| 2012/0101738 A1 | 4/2012 | Boyden et al. | |
| 2012/0107365 A1 | 5/2012 | Colson et al. | |
| 2012/0109613 A1 | 5/2012 | Boyden et al. | |
| 2012/0128783 A1 | 5/2012 | Boyden et al. | |
| 2012/0156499 A1 | 6/2012 | Torchilin et al. | |
| 2012/0174239 A1 | 7/2012 | Anderson et al. | |
| 2012/0177701 A1 | 7/2012 | Ilyinskii et al. | |
| 2012/0184495 A1 | 7/2012 | Koyakutty et al. | |
| 2012/0210450 A1 | 8/2012 | De Sauvage et al. | |
| 2012/0232012 A1 | 9/2012 | Popel et al. | |
| 2012/0263722 A1 | 10/2012 | Ghayur et al. | |
| 2012/0263793 A1 | 10/2012 | Vitaliano | |
| 2012/0272341 A1 | 10/2012 | Combs et al. | |
| 2012/0276133 A1 | 11/2012 | Maldonado | |
| 2012/0276134 A1 | 11/2012 | Fraser et al. | |

(56) References Cited

U.S. PATENT DOCUMENTS

| | | |
|---|---|---|
| 2012/0276155 A1 | 11/2012 | Kishimoto et al. |
| 2012/0276157 A1 | 11/2012 | Fraser et al. |
| 2012/0276158 A1 | 11/2012 | Fraser et al. |
| 2012/0276159 A1 | 11/2012 | Fraser et al. |
| 2012/0276160 A1 | 11/2012 | Maldonado |
| 2014/0303081 A1 | 10/2014 | Dhar et al. |

FOREIGN PATENT DOCUMENTS

| | | |
|---|---|---|
| EP | 2050335 A1 | 4/2009 |
| EP | 2082645 A1 | 7/2009 |
| EP | 1907444 B1 | 8/2009 |
| EP | 1846355 B1 | 12/2009 |
| EP | 2186402 A1 | 5/2010 |
| EP | 2248903 A1 | 11/2010 |
| EP | 2430923 A1 | 3/2012 |
| WO | WO 2000/000503 A1 | 1/2000 |
| WO | WO 2000/045838 A1 | 8/2000 |
| WO | WO 2003/087021 A2 | 10/2003 |
| WO | WO 2003/103581 A2 | 12/2003 |
| WO | WO 2004/096140 A2 | 11/2004 |
| WO | WO 2005/019232 A1 | 3/2005 |
| WO | WO 2005/058028 A2 | 6/2005 |
| WO | WO 2005/079566 A2 | 9/2005 |
| WO | WO 2005/107818 A2 | 11/2005 |
| WO | WO 2005/112619 A2 | 12/2005 |
| WO | WO 2006/026222 A2 | 3/2006 |
| WO | WO 2006/049854 A2 | 5/2006 |
| WO | WO 2006/079014 A2 | 7/2006 |
| WO | WO 2006/079120 A2 | 7/2006 |
| WO | WO 2006/098887 A2 | 9/2006 |
| WO | WO 2006/105403 A2 | 10/2006 |
| WO | WO 2006/107903 A2 | 10/2006 |
| WO | WO 2006/117675 A1 | 11/2006 |
| WO | WO 2006/127987 A2 | 11/2006 |
| WO | WO 2006/128121 A2 | 11/2006 |
| WO | WO 2006/132788 A2 | 12/2006 |
| WO | WO 2007/001962 A2 | 1/2007 |
| WO | WO 2007/014323 A2 | 2/2007 |
| WO | WO 2007/021423 A2 | 2/2007 |
| WO | WO 2007/033215 A2 | 3/2007 |
| WO | WO 2007/040469 A2 | 4/2007 |
| WO | WO 2007/080590 A2 | 7/2007 |
| WO | WO 2007/081608 A2 | 7/2007 |
| WO | WO 2007/101111 A2 | 9/2007 |
| WO | WO 2007/114979 A2 | 10/2007 |
| WO | WO 2007/120818 A2 | 10/2007 |
| WO | WO 2007/131128 A2 | 11/2007 |
| WO | WO 2007/140483 A2 | 12/2007 |
| WO | WO 2008/013952 A2 | 1/2008 |
| WO | WO 2008/019357 A2 | 2/2008 |
| WO | WO 2008/036437 A2 | 3/2008 |
| WO | WO 2008/042469 A2 | 4/2008 |
| WO | WO 2008/048205 A2 | 4/2008 |
| WO | WO 2008/048288 A2 | 4/2008 |
| WO | WO 2008/051291 A2 | 5/2008 |
| WO | WO 2008/085828 A2 | 7/2008 |
| WO | WO 2008/087257 A1 | 7/2008 |
| WO | WO 2008/091465 A2 | 7/2008 |
| WO | WO 2008/091888 A2 | 7/2008 |
| WO | WO 2008/103409 A2 | 8/2008 |
| WO | WO 2008/106646 A2 | 9/2008 |
| WO | WO 2008/127352 A2 | 10/2008 |
| WO | WO 2008/140507 A9 | 11/2008 |
| WO | WO 2008/143633 A2 | 11/2008 |
| WO | WO 2008/147481 A1 | 12/2008 |
| WO | WO 2009/009591 A9 | 1/2009 |
| WO | WO 2009/012303 A2 | 1/2009 |
| WO | WO 2009/023270 A2 | 2/2009 |
| WO | WO 2009/033130 A1 | 3/2009 |
| WO | WO 2009/046446 A2 | 4/2009 |
| WO | WO 2009/047587 A1 | 4/2009 |
| WO | WO 2009/132050 A2 | 10/2009 |
| WO | WO 2010/008995 A2 | 1/2010 |
| WO | WO 2010/011605 A2 | 1/2010 |
| WO | WO 2010/036961 A1 | 4/2010 |
| WO | WO 2010/042823 A1 | 4/2010 |
| WO | WO 2010/054264 A1 | 5/2010 |
| WO | WO 2010/054326 A2 | 5/2010 |
| WO | WO 2010/062413 A1 | 6/2010 |
| WO | WO 2010/074992 A2 | 7/2010 |
| WO | WO 2010/080557 A1 | 7/2010 |
| WO | WO 2010/105058 A1 | 9/2010 |
| WO | WO 2010/111517 A1 | 9/2010 |
| WO | WO 2010/125115 A1 | 11/2010 |
| WO | WO 2010/143942 A1 | 12/2010 |
| WO | WO 2010/148007 A9 | 12/2010 |
| WO | WO 2011/082432 A1 | 7/2011 |
| WO | WO 2011/084620 A1 | 7/2011 |
| WO | WO 2011/084620 A2 | 7/2011 |
| WO | WO 2011/109600 A1 | 9/2011 |
| WO | WO 2011/115602 A1 | 9/2011 |
| WO | WO 2011/119901 A1 | 9/2011 |
| WO | WO 2011/130624 A2 | 10/2011 |
| WO | WO 2011/153348 A2 | 12/2011 |
| WO | WO 2012/061466 A2 | 5/2012 |
| WO | WO 2012/075337 A2 | 6/2012 |
| WO | WO 2012/078745 A1 | 6/2012 |
| WO | WO 2012/092569 42 | 7/2012 |
| WO | WO 2012/106281 A2 | 8/2012 |
| WO | WO 2012/109466 A2 | 8/2012 |
| WO | WO 2012/135848 A2 | 10/2012 |
| WO | WO 2012/138570 A2 | 10/2012 |
| WO | WO 2012/142511 A2 | 10/2012 |
| WO | WO 2012/149252 A2 | 11/2012 |
| WO | WO 2012/149259 A1 | 11/2012 |
| WO | WO 2012/149265 A2 | 11/2012 |
| WO | WO 2012/149282 A2 | 11/2012 |
| WO | WO 2012/149301 A2 | 11/2012 |
| WO | WO 2012/149393 A9 | 11/2012 |
| WO | WO 2012/149405 A2 | 11/2012 |
| WO | WO 2012/149454 A2 | 11/2012 |
| WO | WO 2013/033513 A1 | 3/2013 |
| WO | WO 2014/124425 A1 | 8/2014 |

OTHER PUBLICATIONS

Baas et al., "Slipping Therapeutics to the Mitochondria" SciBX 5(38), Published online Sep. 27, 2012. 4 pages.
Cheng et al., "Formulation of functionalized PLGA-PEG nanoparticles for in vivo targeted drug delivery" Biomaterials, Feb. 2007; 28(5):869-76.
Marrache et al., "Functionalized Polymers for Mitochondria Trafficking of Nanoparticles" Methods Mol Biol, 2015; 1265:103-12.
Sharma et al., "Design and Evaluation of multifunctional nanocarriers for selective delivery of coenzyme Q10 to Mitochondria" Biomacromolecules, Jan. 9, 2012; 13(1):239-52. Published online Dec. 16, 2011.
International Search Report/Written Opinion for PCT/US2013/026299, dated Apr. 12, 2013. 9 pages total.
International Preliminary Report on Patentability for PCT US2013/026299, dated Aug. 28, 2014. 2 pages total.
Agemy et al. "Targeted nanoparticle enhanced proapoptotic peptide as potential therapy for glioblastoma" 2011. *Proc Natl Acad Sci USA*. 108(42):17450-17455.
Butera et al. "Peptidic targeting of phosphatidylserine for the MRI detection of apoptosis in atherosclerotic plaques". 2009. *Mol. Pharm.* 6:1903-1919.
Chalmers et al. "Selective uncoupling of individual mitochondria within a cell using a mitochondria-targeted photoactivated protonophore" 2012. *J. Am Chem Soc.* 134(2):758-761.
Dhar et al. "Targeted delivery of a cisplatin prodrug for safer and more effective prostate cancer therapy in vivo". 2011. *Proc.Natl. Acad.Sci. USA*. 108(5):1850-1855.
Fulda et al. "Targeting Mitochondria for cancer therapy". 2010. *Nature Reviews—Drug Discovery.* 9:447.
Gomes et al. "Characterization of PLGA microparticles as a drug carrier for 3-ethoxycarbonyl-2h-benzofuro[3,2-f]-1-benzopyran-2-one. Ultrastructural study of cellular uptake and intracellular distribution" 2006. *Drug Deliv.* 13(6):447-454.

(56) References Cited

OTHER PUBLICATIONS

Gosh et al. "Nanocapsulated curcumin: oral chemopreventive formulation against diethylnitrosamine induced hepatocellular carcinoma in rat". 2012. *Chem. Biol. Interact.* 195(3):206-214.
Hoye et al. "Targeting mitochondria". 2008. *Acc Chem Res.* 41(1):87-97.
International Patent Application No. PCT/US2013/026299, filed Feb. 15, 2013; International Search Report / Written Opinion dated Apr. 12, 2013; 9 pages.
International Patent Application No. PCT/US2013/026299, filed Feb. 15, 2013; International Preliminary Report on Patentability dated Aug. 28, 2014; 2 pages.
Kolishetti et al. "Engineering of self-assembled nanoparticle platform for precisely controlled combination drug therapy" 2010. *Proc.Natl.Acad.Sci.USA.* 107(42):17939-17944.
Marrache et al. "Engineering of blended nanoparticle platform for delivery of mitochondria-acting therapeutics" 2012. *Proc Natl. Acad Sci USA,* 109(40):16288-16293.
Marrache et al. "Engineered Nanoparticles for Mitochondria Trafficking of Drugs". 4 pages.
Melo et al. "Nanocytotoxicity: violacein and violacein-loaded poly (D, L-lactide-co-glycolide) nanoparticles acting on human leukemic cells". 2009. *J. Biomed Nanotechnol.* 5(2):192-201.
Murphy et al. "Targeting antioxidants to mitochondria by conjugation to lipophilic cations". 2007. *Annu Rev Pharmacol Toxicol.* 47:629-656.

Porteous et al. "Rapid uptake of lipophilic triphenylphosphonium cations by mitochondria in vivo following intravenous injection: implications for mitochondria-specific therapies and probes", 2010. *Biochim Biophys Acta.* 1800(9):1009-1017.
Prime et al. "A mitochondria-targeted S-nitrosothiol modulates respiration, nitrosates thiols, and protects against ischemia-reperfusion injury" 2009. *Proc Natl Acad Sci USA.* 106(26):10765-10769.
Ross et al. "Lipophilic triphenylphosphonium cations as tools in mitochondrial bioenergetics and free radical biology" 2005. *Biochemistry (Mosc),* 70(2):222-230.
Salvador-Morales et al. "Immuncompatibility Properties of Lipid-Polymer Hybrid Nanoparticles with Heterogeneous Surface Functional Groups". 2009. *Biomaterials.* 30:2231-2240.
Smith et al. "Delivery of bioactive molecules to mitochondria in vivo". 2003. *Proc Natl Acad Sci USA.* 100(9):5407-5412.
Smith et al. "Selective targeting of an antioxidant to mitochondria". 1999. *Eur J. Biochem.* 263(3):709-716.
Swamakar et al. "Oral bioavailability, therapeutic efficacy and reactive oxygen species scavenging properties of coenzyme Q10-loaded polymeric nanoparticles". 2011. *Biomaterials.* 32(28):6860-6874.
Wang et al. "Alpha-tocopheryl polyethylene glycol succinate-emulsified poly(lactic-co-glycolic acid) nanoparticles for reversal of multidrug resistance in vitro". *Nanotechnology.* 2012. 23(49):495103.
Weiss et al., "Coupling of biotin-(poly(ethylene glycol))amine to poly(D,L-lactide-co-glycolide) nanoparticles for versatile surface modification" Bioconjug Chem, Jul.-Aug. 2007; 18(4):1087-94. Published Online Jun. 23, 2007.

\* cited by examiner

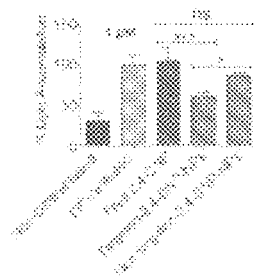 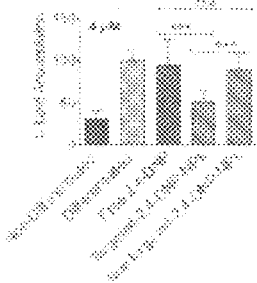 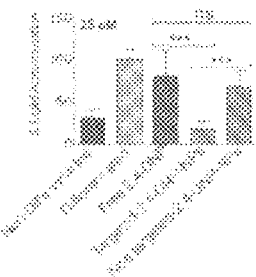 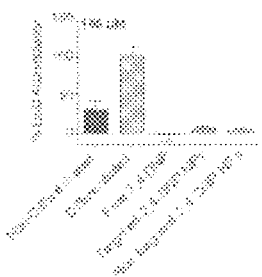
FIG. 12A    FIG. 12B    FIG. 12C    FIG. 12D
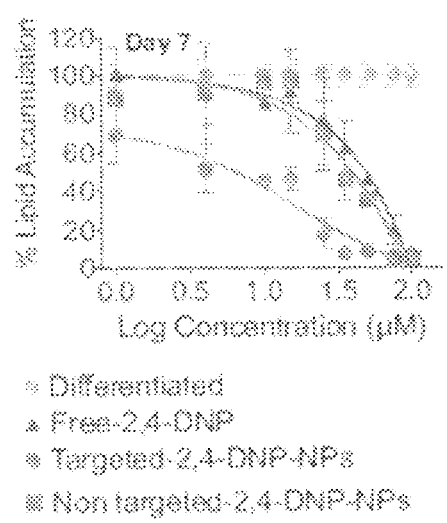
FIG. 13

| Dose (mg/animal) | Dose (mg/kg) | AUC$_{(0-24h)}$ (ng/mL) | C$_{max}$ (ng/mL) | 2-Compartment Model[1] | | | | |
|---|---|---|---|---|---|---|---|---|
| | | | | Central Compartment (Initial Phase) | | | Periphery Compartment (Terminal Phase, at 24 h) | |
| | | | | Volume of Distribution, central compartment (mL) | Clearance, t=0 (mL/h) | t$_{1/2}$ (h) | Volume of Distribution, terminal (mL) | Clearance, terminal (mL/h) |
| 24.19 ± 0.28 | 81.43 ± 0.14 | 34,784.5 ± 2,117.3 | 3,237.5 ± 128.2 | 7.48 ± 0.31 | 1.40 ± 0.25 | 2.40 ± 0.77 | 2.49 ± 0.31 | 0.016 ± 0.021 |

[1] Least-squares fit to model: C = A*exp{-k$_1$*t} + B*exp{-k$_2$*t};
AUC: Area under curve
t$_{1/2}$: Elimination half-life
C$_{max}$: The peak plasma concentration of nanoparticle after administration Values reported as: (group mean) ± (standard deviation)

FIG. 15

NANOPARTICLES FOR MITOCHONDRIAL TRAFFICKING OF AGENTS

RELATED APPLICATIONS

This application is the § 371 U.S. National Stage of International Application No. PCT/US2013/026299, filed 15 Feb. 2013, which claims the benefit of priority to U.S. Provisional Patent Application No. 61/600,088, filed on Feb. 17, 2012, each of which application are hereby incorporated herein in their entireties to the extent that it does not conflict with the present disclosure.

STATEMENT OF GOVERNMENTAL SUPPORT

This invention was made with government support under grant number P30GM092378, awarded by the National Institutes of Health of the United States government. The government has certain rights in the invention.

FIELD

The present disclosure relates to nanoparticles configured to traffic agents to mitochondria and methods of use thereof, including diagnostic and therapeutic uses.

BACKGROUND

Mitochondrial dysfunction can play a role in a variety of disorders, including cancer, neurodegenerative and neuromuscular disease, obesity and diabetes. One major challenge in treating such diseases is not the development of effective drugs, but rather the distribution of the drugs to the mitochondria. The ability to deliver drugs to mitochondria in sufficient amounts while avoiding toxicity remains a challenge.

SUMMARY

The present disclosure describes, among other things, nanoparticles configured to traffic agents to mitochondria. By trafficking agents to mitochondria, as opposed to the cytoplasm or other organelles of cells, the relative concentration of the agents in the mitochondria may be increased to enhance the effect of the agent on the mitochondria while decreasing the effect at other locations. Accordingly, efficacy may be enhanced while side effects or toxicity may be diminished. The agents to be delivered to the mitochondria may be therapeutic agents, diagnostic agents, or the like.

As described herein, the size and surface charge density of the nanoparticle affect the ability to target the nanoparticle to the mitochondria. For example, nanoparticles having diameters of about 200 nanometers or less are found to more readily accumulate in the mitochondria than nanoparticles having diameters greater than about 200 nanometers. Nanoparticles having a zeta potential of about 0 or greater are found to more readily accumulate in the mitochondria than nanoparticles having zeta potentials of less than about zero.

In embodiments, nanoparticles described herein include a hydrophobic core and a hydrophilic layer surrounding the core. The nanoparticles also include a mitochondrial targeting moiety. The nanoparticles have a diameter of about 200 nanometers or less and have a zeta potential of about 0 mV or greater, such as about 1 mV or greater, about 7 mV or greater, about 20 mV or greater, about 25 mV or greater, about 30 mV or greater, about 34 mV or greater, about 35 mV or greater, or the like. Such nanoparticles may allow for targeting of agents associated with the nanoparticles to mitochondria, which may, in embodiments in which the nanoparticles include one or more therapeutic agents, allow for treatment of diseases associated with mitochondrial dysfunction.

Advantages of one or more of the various embodiments presented herein over prior nanoparticles, imaging methodologies, treatment modalities, or the like will be readily apparent to those of skill in the art based on the following detailed description when read in conjunction with the accompanying drawings.

BRIEF DESCRIPTION OF THE DRAWINGS

FIGS. 12A-D are bar graphs showing that mouse 3T3-L1 preadipocytes were differentiated into adipocytes in the presence of 1 μM (A), 4 μM (B), 25 μM (C), or 1.00 μM (D) of targeted 2,4-DNP nanoparticles, nontargeted 2,4-DNP nanoparticles, and free 2,4-DNP for 7 d. Nondifferentiated cells and completely differentiated cells were used as controls. Intracellular lipids were stained with AdipoRed (Lonza), and percent lipid accumulation was calculated. Inhibition of adipocyte differentiation is shown for day 7. Statistical analyses were performed using one-way ANOVA with Tukey's post hoc test. *P<0.05; ***P<0.001. Similar results were obtained from two independent experiments. ns, nonsignificant.

FIG. 13 is a graph showing results presented in FIGS. 12A-D in a different format.

FIG. 15 is a table showing pharmacokinetic data of targeted nanoparticles in rats.

Figure 1:
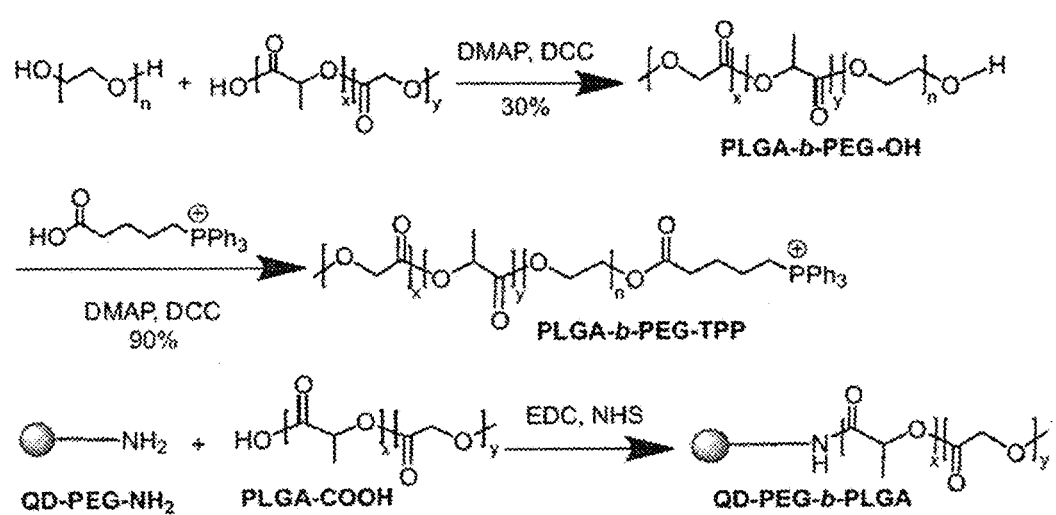
FIG. 1 is schematic drawing illustration reaction schemes for the synthesis of PLGA-b-PEG-OH, PLGA-b-PEG-TPP, and QD-conjugated polymer.

The schematic drawings in are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like.

As used herein, "disease" means a condition of a living being or one or more of its parts that impairs normal functioning. As used herein, the term disease encompasses terms such disease, disorder, condition, dysfunction and the like.

As used herein, "treat" or the like means to cure, prevent, or ameliorate one or more symptom of a disease.

As used herein, a disease associated with a mitochondrial dysfunction is a disease that may be treated by therapeutic action on or within mitochondria, such as by delivering a therapeutic agent to the mitochondria and the agent interacting with one or more molecule on or in the mitochondria.

As used herein, a compound that is "hydrophobic" is a compound that is insoluble in water or has solubility in water below 1 milligram/liter.

As used herein a compound that is "hydrophilic" is a compound that is water soluble or has solubility in water above 1 milligram/liter.

As used herein, "bind," "bound," or the like means that chemical entities are joined by any suitable type of bond, such as a covalent bond, an ionic bond, a hydrogen bond, van der walls forces, or the like. "Bind," "bound," and the like are used interchangeable herein with "attach," "attached," and the like.

As used herein, a molecule or moiety "attached" to a core of a nanoparticle may be embedded in the core, contained within the core, attached to a molecule that forms at least a portion of the core, attached to a molecule attached to the core, or directly attached to the core.

As used herein, a "derivative" of a compound is a compound structurally similar to the compound of which it is a derivative. Many derivatives are functional derivatives. That is, the derivatives generally a desired function similar to the compound to which it is a derivative. By way of example, triphenyl phosophonium (TPP) is described herein as a mitochondrial targeting moiety because it can accumulate, or cause a compound or complex (such as a nanoparticle) to which it is bound to accumulate, in the mitochondria. Accordingly, a functional derivative of TPP is a derivative of TPP that may accumulate, or cause a compound or complex to which it is bound to accumulate, in the mitochondria in a similar concentration as TPP (e.g., within about a 100 fold concentration range, such as within about a 10 fold concentration range).

Nanoparticles, as described herein, include, in embodiments, a hydrophobic core, a hydrophilic layer surrounding the core, and one or more mitochondrial targeting moieties, as well as one or more diagnostic agents or one or more therapeutic agents. In embodiments, the contrast agents or therapeutic agents are contained or embedded within the core. If the nanoparticle includes therapeutic agents, the agents are preferably released from the core at a desired rate. In embodiments, the core is biodegradable and releases the agents as the core is degraded or eroded. The targeting moieties preferably extend outwardly from the core so that they are available for interaction with cellular components or so that they affect surface properties of the nanoparticle, which interactions or surface properties will favor preferential distribution to mitochondria. The targeting moieties may be tethered to the core or components that interact with the core.

I. Core

The core of the nanoparticle may be formed from any suitable component or components. Preferably, the core is formed from hydrophobic components such as hydrophobic polymers or hydrophobic portions of polymers. The core may also or alternatively include block copolymers that have hydrophobic portions and hydrophilic portions that may self-assemble in an aqueous environment into particles having the hydrophobic core and a hydrophilic outer surface. In embodiments, the core comprises one or more biodegradable polymer or a polymer having a biodegradable portion.

Any suitable synthetic or natural bioabsorbable polymers may be used. Such polymers are recognizable and identifiable by one or ordinary skill in the art. Non-limiting examples of synthetic, biodegradable polymers include: poly(amides) such as poly(amino acids) and poly(peptides); poly(esters) such as poly(lactic acid), poly(glycolic acid), poly(lactic-co-glycolic acid) (PLGA), and poly(caprolactone); poly(anhydrides); poly(orthoesters); poly(carbonates); and chemical derivatives thereof (substitutions, additions of chemical groups, for example, alkyl, alkylene, hydroxylations, oxidations, and other modifications routinely made by those skilled in the art), fibrin, fibrinogen, cellulose, starch, collagen, and hyaluronic acid, copolymers and mixtures thereof. The properties and release profiles of these and other suitable polymers are known or readily identifiable.

In various embodiments, described herein the core comprises PLGA. PLGA is a well-known and well-studied hydrophobic biodegradable polymer used for the delivery and release of therapeutic agents at desired rates.

Preferably, the at least some of the polymers used to form the core are amphiphilic having hydrophobic portions and hydrophilic portions. The hydrophobic portions can form the core, while the hydrophilic regions may form a layer surrounding the core to help the nanoparticle evade recognition by the immune system and enhance circulation half-life. Examples of amphiphilic polymers include block copolymers having a hydrophobic block and a hydrophilic block. In embodiments, the core is formed from hydrophobic portions of a block copolymer, a hydrophobic polymer, or combinations thereof.

The ratio of hydrophobic polymer to amphiphilic polymer may be varied to vary the size of the nanoparticle. In embodiments, a greater ratio of hydrophobic polymer to amphiphilic polymer results in a nanoparticle having a larger diameter. Any suitable ratio of hydrophobic polymer to amphiphilic polymer may be used. In embodiments, the nanoparticle includes about a 50/50 ratio by weight of amphiphilic polymer to hydrophobic polymer or ratio that includes more amphiphilic polymer than hydrophilic polymer, such as about 20/80 ratio, about a 30/70 ratio, about a 40/60 ratio, about a 55/45 ratio, about a 60/40 ratio, about a 65/45 ratio, about a 70/30 ratio, about a 75/35 ratio, about a 80/20 ratio, about a 85/15 ratio, about a 90/10 ratio, about a 95/5 ratio, about a 99/1 ratio, or about 100% amphiphilic polymer.

In embodiments, the hydrophobic polymer comprises PLGA, such as PLGA-COOH or PLGA-OH or PLGA-TPP. In embodiments, the amphiphilic polymer comprises PLGA and PEG, such as PLGA-PEG. The amphiphilic polymer may be a dendritic polymer having branched hydrophilic portions. Branched polymers may allow for attachment of more than moiety to terminal ends of the branched hydrophilic polymer tails, as the branched polymers have more than one terminal end.

As described herein, nanoparticles having a diameter of about 250 nm or less; e.g. about 200 nm or less, are generally more effectively targeted to mitochondria than nanoparticles having a diameter of greater than about 250 nm or greater than about 200 nm. In embodiments, a nanoparticle effective for mitochondrial targeting has a diameter of about 190 nm or less, about 180 nm or less, about 170 nm or less, about 160 nm or less, about 150 nm or less, about 140 nm or less, about 130 nm or less, about 120 nm or less, about 110 nm or less, about 100 nm or less, about 90 nm or less, about 80 nm or less, about 70 nm or less, about 60 nm or less, about 50 nm or less, about 40 nm or less, about 30 nm or less, about 20 nm or less, or about 10 nm or less. In embodiments, a nanoparticle has a diameter of from about 10 nm to about 250 nm, such as from about 20 nm to about 200 nm, from about 50 nm to about 160 nm, from about 60 nm to about 150 nm, from about 70 nm to about 130 nm, from about 80 nm to about 120 nm, from about 80 nm to about 100 nm, or the like.

II. Hydrophilic Layer Surrounding the Core

The nanoparticles described herein may optionally include a hydrophilic layer surrounding the hydrophilic core. The hydrophilic layer may assist the nanoparticle in evading recognition by the immune system and may enhance circulation half-life of the nanoparticle.

As indicated above, the hydrophilic layer may be formed, in whole or in part, by a hydrophilic portion of an amphiphilic polymer, such as a block co-polymer having a hydrophobic block and a hydrophilic block.

Any suitable hydrophilic polymer or hydrophilic portion of an amphiphilic polymer may form the hydrophilic layer or portion thereof. The hydrophilic polymer or hydrophilic portion of a polymer may be a linear or branched or dendritic polymer. Examples of suitable hydrophilic polymers include polysaccharides, dextran, chitosan, hyaluronic acid, polyethylene glycol, polymethylene oxide, and the like.

In embodiments, a hydrophilic portion of a block copolymer comprises polyethylene glycol (PEG). In embodiments, a block copolymer comprises a hydrophobic portion comprising PLGA and a hydrophilic portion comprising PEG.

A hydrophilic polymer or hydrophilic portion of a polymer may contain moieties that are charged under physiological conditions, which may be approximated by a buffered saline solution, such as a phosphate or citrate buffered saline solution, at a pH of about 7.4, or the like. Such moieties may contribute to the charge density or zeta potential of the nanoparticle. Zeta potential is a term for electro kinetic potential in colloidal systems. While zeta potential is not directly measurable, it can be experimentally determined using electrophoretic mobility, dynamic electrophoretic mobility, or the like.

As indicated herein, zeta potential plays a role in the ability of nanoparticles to accumulate in mitochondria, with higher zeta potentials generally resulting in increased accumulation in the mitochondria. In embodiments, the nanoparticles have a zeta potential, as measured by dynamic light scattering, of about 0 mV or greater. For example, a nanoparticle may have a zeta potential of about 1 mV or greater, of about 5 mV or greater, of about 7 mV or greater, or about 10 mV or greater, or about 15 mV or greater, of about 20 mV or greater, about 25 mV or greater, about 30 mV or greater, about 34 mV or greater, about 35 mV or greater, or the like. In embodiments, a nanoparticle has a zeta potential of from about 0 mV to about 100 mV, such as from about 1 mV to 50 mV, from about 2 mV to about 40 mV, from about 7 mV to about 35 mV, or the like.

Any suitable moiety that may be charged under physiological conditions may be a part of or attached to a hydrophilic polymer or hydrophilic portion of a polymer. In embodiments, the moiety is present at a terminal end of the polymer or hydrophilic portion of the polymer. Of course, the moiety may be directly or indirectly bound to the polymer backbone at a location other than at a terminal end. Due to the substantial negative electrochemical potential maintained across the inner mitochondrial membrane, cations, particularly if delocalized, are effective at crossing the hydrophobic membranes and accumulating in the mitochondrial matrix. Cationic moieties that are known to facilitate mitochondrial targeting are discussed in more detail below. However, cationic moieties that are not particularly effective for selective mitochondrial targeting may be included in nanoparticles or be bound to hydrophilic polymers or portions of polymers. In embodiments, anionic moieties may form a part of or be attached to the hydrophilic polymer or portion of a polymer. The anionic moieties or polymers containing the anionic moieties may be included in nanoparticles to tune the zeta potential, as desired. In embodiments, a hydrophilic polymer or portion of a polymer includes a hydroxyl group that can result in an oxygen anion when placed in a physiological aqueous environment. In embodiments, the polymer comprises PEG-OH where the OH serves as the charged moiety under physiological conditions.

III. Mitochondria Targeting Moieties

The nanoparticles described herein include one or more moieties that target the nanoparticles to mitochondria. As used herein, "targeting" a nanoparticle to mitochondria means that the nanoparticle accumulates in mitochondria relative to other organelles or cytoplasm at a greater concentration than substantially similar non-targeted nanoparticle. A substantially similar non-target nanoparticle includes the same components in substantially the same relative concentration (e.g., within about 5%) as the targeted nanoparticle, but lacks a targeting moiety.

The mitochondrial targeting moieties may be tethered to the core in any suitable manner, such as binding to a molecule that forms part of the core or to a molecule that is bound to the core. In embodiments, a targeting moiety is bound to a hydrophilic polymer that is bound to a hydrophobic polymer that forms part of the core. In embodiments, a targeting moiety is bound to a hydrophilic portion of a block copolymer having a hydrophobic block that forms part of the core.

The targeting moieties may be bound to any suitable portion of a polymer. In embodiments, the targeting moieties are attached to a terminal end of a polymer. In embodiments, the targeting moieties are bound to the backbone of the polymer, or a molecule attached to the backbone, at a location other than a terminal end of the polymer. More than one targeting moiety may be bound to a given polymer. In embodiments, the polymer is a dendritic polymer having multiple terminal ends and the targeting moieties may be bound to more than one of terminal ends.

The polymers, or portions thereof, to which the targeting moieties are bound may contain, or be modified to contain, appropriate functional groups, such as —OH, —COOH, —NH$_2$, —SH, —N$_3$, —Br, —Cl, —I, —CH═CH$_2$, C≡CH, —CHO or the like, for reaction with and binding to the targeting moieties that have, or are modified to have, suitable functional groups.

Examples of targeting moieties tethered to polymers presented throughout this disclosure for purpose of illustrating the types of reactions and tethering that may occur. However, one of skill in the art will understand that tethering of targeting Moieties to polymers may be carried out according to any of a number of known chemical reaction processes.

Targeting moieties may be present in the nanoparticles at any suitable concentration. In embodiments, the concentration may readily be varied based on initial in vitro analysis to optimize prior to in vivo study or use. In embodiments, the targeting moieties will have surface coverage of from about 5% to about 100%.

Any suitable moiety for facilitating accumulation of the nanoparticle within the mitochondria may be employed. Due to the substantial negative electrochemical potential maintained across the inner mitochondrial membrane, delocalized lipophilic cations are effective at crossing the hydrophobic membranes and accumulating in the mitochondria. Triphenyl phosphonium (TPP) containing compounds can accumulate greater than 10 fold within the mitochondrial matrix. Any suitable TPP-containing compound may be used as a mitochondrial matrix targeting moiety. Representative examples of TPP-based moieties may have structures indicated below in Formula I, Formula II or Formula III:

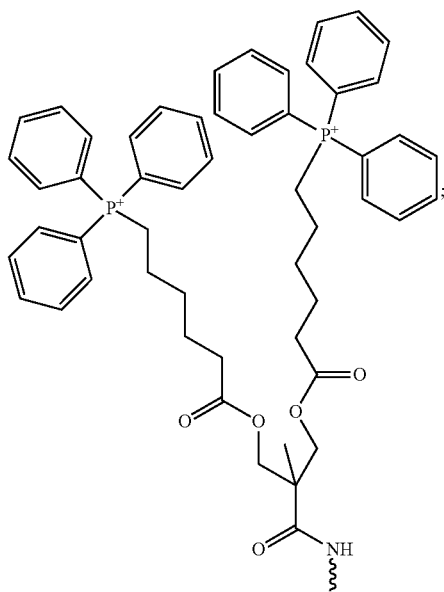

I

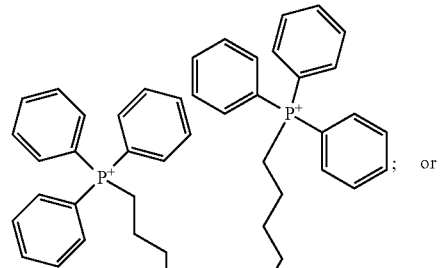

II

; or

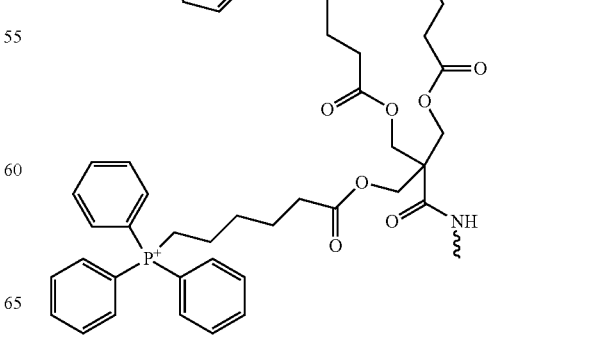

-continued

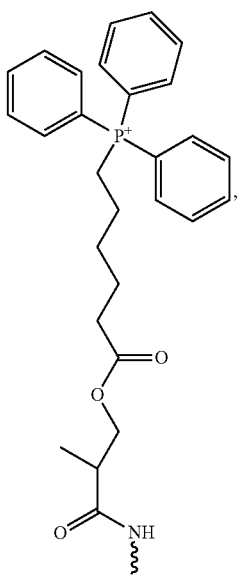

III where the amine (as depicted) may be conjugated to a polymer or other component for incorporation into the nanoparticle.

In embodiments, the delocalized lipophilic cation for targeting the mitochondrial matrix is a rhodamine cation, such as Rhodamine 123 having Formula IV as depicted below:

IV

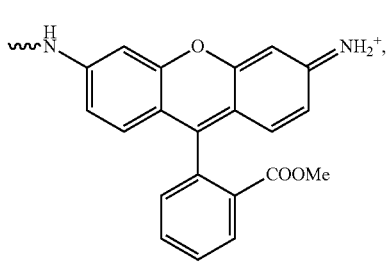

where the secondary amine (as depicted) may be conjugated to a polymer, lipid, or the like for incorporation into the nanoparticle.

Of course, non-cationic compounds may serve to target and accumulate in the mitochondrial matrix. By way of example, Szeto-Shiller peptide may serve to target and accumulate a nanoparticle in the mitochondrial matrix. Any suitable Szetto-Shiller peptide may be employed as a mitochondrial matrix targeting moiety. Non-limiting examples of suitable Szeto-Shiller peptides include SS-02 and SS-31, having Formula V and Formula VI, respectively, as depicted below:

V

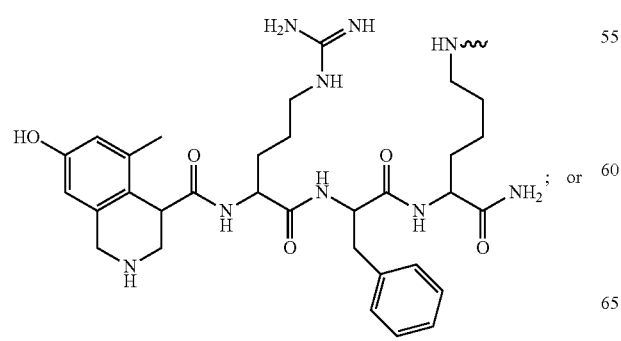

; or

-continued

VI

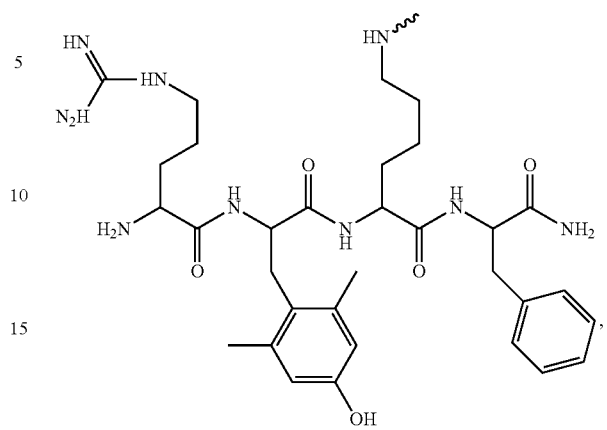

, where the secondary amine (as depicted) may be conjugated to a polymer, lipid, or the like for incorporation into the nanoparticle.

For purposes of example, a reaction scheme for synthesis of PLGA-PEG-TPP is shown below in Scheme 1. It will be understood that other schemes may be employed to synthesize PLGA-PEG-TPP and that similar reaction schemes may be employed to tether other mitochondrial targeting moieties to PLGA-PEG or to tether moieties to other polymer or components of a nanoparticle.

(Scheme I)

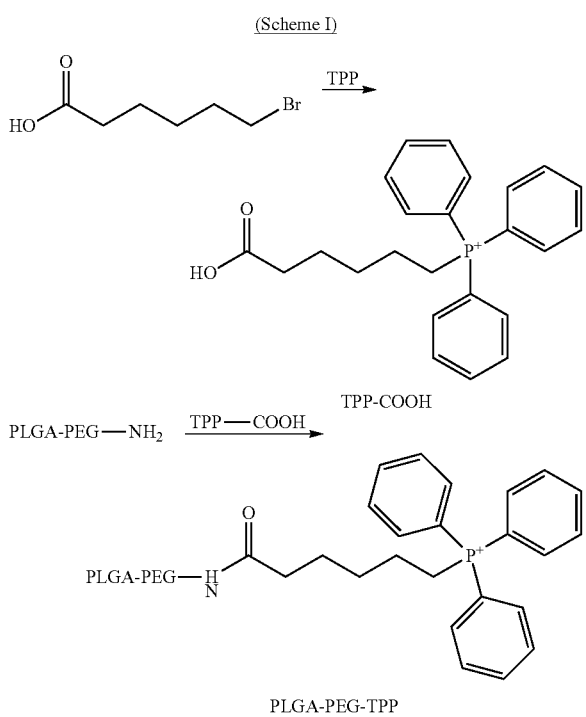

Preferably, a targeting moiety is attached to a hydrophilic polymer or hydrophilic portion of a polymer so that the targeting moiety will extend from the core of the nanoparticle to facilitate the effect of the targeting moiety.

It will be understood that the mitochondrial targeting moiety may alter the zeta potential of a nanoparticle. Accordingly, the zeta potential of a nanoparticle may be tuned by adjusting the amount of targeting moiety included in the nanoparticle. The zeta potential may also be adjusted by including other charged moieties, such as charged moieties of, or attached to, hydrophilic polymers or hydrophilic portions of polymers.

In embodiments, charged moieties are provided only by, or substantially by, mitochondrial targeting moieties. In embodiments, about 95% or more of the charged moieties are provided by mitochondrial targeting moieties. In embodiments, about 90% or more of the charged moieties are provided by mitochondrial targeting moieties. In embodiments, about 85% or more of the charged moieties are provided by mitochondrial targeting moieties. In embodiments, about 80% or more of the charged moieties are provided by mitochondrial targeting moieties. In embodiments, about 75% or more of the charged moieties are provided by mitochondrial targeting moieties. In embodiments, about 70% or more of the charged moieties are provided by mitochondrial targeting moieties. In embodiments, about 65% or more of the charged moieties are provided by mitochondrial targeting moieties. In embodiments, about 60% or more of the charged moieties are provided by mitochondrial targeting moieties. In embodiments, about 55% or more of the charged moieties are provided by mitochondrial targeting moieties. In embodiments, about 5% or more of the charged moieties are provided by mitochondrial targeting moieties. Of course, the mitochondrial targeting moieties may provide any suitable amount or percentage of the charged moieties.

In embodiments, the nanoparticles are formed by blending a polymer that include a mitochondrial targeting moiety with a polymer that includes a charged moiety other than a mitochondrial targeting moiety.

IV. Therapeutic Agents

A nanoparticle, as described herein, may include any one or more therapeutic agent. The therapeutic agent may be embedded in, or contained within, the core of the nanoparticle. Preferably, the therapeutic agent is released from the core at a desired rate. If the core is formed from a polymer (such as PLGA) or combination of polymers having known release rates, the release rate can be readily controlled.

In embodiments, a therapeutic agent or precursor thereof is conjugated to a polymer, or other component of a nanoparticle, in a manner described above with regard to targeting moieties. The therapeutic agent may be conjugated via a cleavable linker so that the agent may be released when the nanoparticle reaches the target location, such as mitochondria.

The therapeutic agents may be present in the nanoparticle at any suitable concentration. For example, a therapeutic agent may be present in the nanoparticle at a concentration from about 0.01% to about 30% by weight of the nanoparticle.

In embodiments, the nanoparticle includes one or more therapeutic agent useful for treatment of a disease associated with mitochondrial dysfunction. Such diseases include neurodegenerative disease, obesity, and cancer. Examples of neurodegenerative diseases may be associated with mitochondrial dysfunction include Alzheimer's disease, ischemic injury, Parkinson diseases, stroke, and the like. Examples of types of cancer that may be associated with mitochondrial dysfunction include cancers of breast, prostate, colon, melanoma, lymphoma, and the like.

In embodiments, the nanoparticle includes one or more therapeutic agent configured to reduce amounts of amyloid beta. For example, the therapeutic agent may be curcumin, other antioxidants, folic acid, lacmoid, or the like.

In embodiments, the nanoparticle includes one or more mitochondrial uncoupler that acts to separate oxidative phosphorylation from ATP synthesis. For example, the therapeutic agent may be 2,4-dinitrophenol (DNP), or the like.

In embodiments, the nanoparticle includes one or more mitochondrial acting anti-cancer agent. For example, the therapeutic agent may be (i) a modulator of the BCL-3 protein family, such as compounds that act on BCL-$X_L$, BCL-2, BCL-W, MCL1, or the like; (ii) metabolic inhibitors such as compounds that affect, HK, affect HK2-VDAC interaction, PDK inhibitors, affect LDH-A, affect fatty acid synthase, affect ATP citrate lyase, acetyl-CoA carboxylase inhibitors, or the like; (iii) VDAC-targeting or ANT-targeting agents; (iv) ROS regulators such as SOD inhibitors, GSH inhibitors, GPX inhibitors, or the like; (v) HSP90 inhibitor; or (vi) the like. Examples of specific mitochondrial acting anti-cancer agents include lonidamine (LND), α-tocopheryl succinate (α-TOS), dichloroacetate, A-385358, ABT-263, ABT-737, AT-101, 2-amino-6-bromo-4-(1-cyano-2-ethoxy-2-oxoethyl)-4H-chromene-3-carboxylate (HA14-1), oblimersen, obatoclax, gossypol, methyl jasmonate, dichloroacetate, HK2 peptide, LDH-A shRNA, orlistat, SB-204990, soraphen A, 4-(N-(s-glutathionylacetate)aminophenylarsenoxide (GSAO), clodronate, PK11195, menadione, β-lapachone, CD437, gamitrinibs, 8-(2-chloro-3,4,5-trimethyoxybenzyl)-2-fluoro-9-(pent-4-nyl)-9H-purin-6-amine (PU24Fcl), (8-(6-bromobenzo[d][1,3]dioxol-5-ylthio)-9-(pent-4-ynyl)-9H-purin-6-amine (PU—H58), 8-(6-iodobenzo[d][1,3]dioxol-5-ylthio)-9-(3-isopropylamio)propyl-9H-purin-6-amine (PU—H71), shepherdin, reservatrol, 2-methoxyestradiol, tetrathiomolybdate (ATN-224), buthionine sulphoximine, dimethylamino-parthenolide (DMAPT), parthenolide, imexons, mangafodipir, menadione, motexafin gadolinium, PEITCs, elescomol (STA-4783), all-trans-retinoic acid, 6-[3-(1-adamantyl)-4-hydroxyphenyl]-2-napthalene carboxylic acid (CD437), (E)-3-(4'-hydroxy-3'-adamantylbiphenyl-4yl)acrylic acid (ST1926), 3-bromopyruvate, butyric acid, resveratrol, 2-deoxy-D-glucose, arsenite trioxide, betulinic acid, and the like. One or more compounds or classes of compounds described in, for example, Fulda et al., targeting mitochondria for cancer therapy, Nature Reviews-Drug Discovery, volume 9: 447 (June 2010) may be used.

V. Contrast Agents

A nanoparticle as described herein may include one or more contrast agents for purpose of imaging, visualization or diagnosis. In embodiments, imaging is performed to verifying that therapeutic nanoparticles are being properly trafficked to mitochondria. Any suitable contrast agent may be employed. In embodiments, the contrast agent is suitable for in vivo magnetic resonance imaging (MRI), such as iron oxide (IO) nanocrystals or gadolinium complexes. In embodiments, the contrast agent is suitable for ex vivo/in vivo optical imaging, such as quantum dot (QD) (fluorescence) or fluorescent dyes, cdots, pdots, or the like. In embodiments, the nanoparticle includes both contrast agents for MRI and agents for fluorescent optical imaging.

Contrast agents may be incorporated into the nanoparticle in any suitable manner. In embodiments, the contrast agents are incorporated into the core or are contained within the core. In embodiments, the contrast agents are tethered to a polymer or other component of the nanoparticle. Such tethering can be carried out as described above with regard to other components of the nanoparticle, such as targeting moieties.

Contrast agents may be present in a nanoparticle in any suitable amount. In embodiments, a contrast agent is present in a nanoparticle from about 0.05% by weight to about 30% by weight of the nanoparticle.

VI. Synthesis of Nanoparticle

Nanoparticles, as described herein, may be synthesized or assembled via any suitable process. Preferably, the nanoparticles are assembled in a single step to minimize process variation. A single step process may include nanoprecipitation and self-assembly.

In general, the nanoparticles may be synthesized or assembled by dissolving or suspending hydrophobic components in an organic solvent, preferably a solvent that is miscible in an aqueous solvent used for precipitation. In embodiments, acetonitrile is used as the organic solvent, but any suitable solvent such as dimethlyformamide (DMF), dimethyl sulfoxide (DMSO), acetone, or the like may be used. Hydrophilic components are dissolved in a suitable aqueous solvent, such as water, 4 wt-% ethanol, or the like. The organic phase solution may be added drop wise to the aqueous phase solution to nanoprecipitate the hydrophobic components and allow self-assembly of the nanoparticle in the aqueous solvent.

A process for determining appropriate conditions for forming the nanoparticles may be as follows. Briefly, functionalized polymers and other components, if included or as appropriate, may be co-dissolved in organic solvent mixtures. This solution may be added drop wise into hot (e.g., 65° C.) aqueous solvent (e.g, water, 0.4 wt-% ethanol, etc.), whereupon the solvents will evaporate, producing nanoparticles with a hydrophobic core surrounded by a hydrophilic polymer component, such as PEG. Once a set of conditions where a high (e.g., >75%) level of targeting moiety surface loading has been achieved, contrast agents or therapeutic agents may be included in the nanoprecipitation and self-assembly of the nanoparticles.

If results are not desirably reproducible by manual mixing, microfluidic channels may be used.

Nanoparticles may be characterized for their size, charge, stability, IO and QD loading, drug loading, drug release kinetics, surface morphology, and stability using well-known or published methods.

Nanoparticle properties may be controlled by (a) controlling the composition of the polymer solution, and (b) controlling mixing conditions such as mixing time, temperature, and ratio of water to organic solvent. The likelihood of variation in nanoparticle properties increases with the number of processing steps required for synthesis.

The size of the nanoparticle produced can be varied by altering the ratio of hydrophobic core components to amphiphilic shell components. Nanoparticle size can also be controlled by changing the polymer length, by changing the mixing time, and by adjusting the ratio of organic to the phase. Prior experience with nanoparticles from PLGA-b-PEG of different lengths suggests that nanoparticle size will increase from a minimum of about 20 nm for short polymers (e.g. $PLGA_{3000}$-$PEG_{750}$) to a maximum of about 150 nm for long polymers (e.g. $PLGA_{100,000}$-$PEG_{10,000}$). Thus, molecular weight of the polymer will serve to adjust the size.

Nanoparticle surface charge can be controlled by mixing polymers with appropriately charged end groups. Additionally, the composition and surface chemistry can be controlled by mixing polymers with different hydrophilic polymer lengths, branched hydrophilic polymers, or by adding hydrophobic polymers.

Once formed, the nanoparticles may be collected and washed via centrifugation, centrifugal ultrafiltration, or the like. If aggregation occurs, nanoparticles can be purified by dialysis, can be purified by longer centrifugation at slower speeds, can be purified with the use surfactant, or the like.

Once collected, any remaining solvent may be removed and the particles may be dried, which should aid in minimizing any premature breakdown or, release of components. The nanoparticles may be freeze dried with the use of bulking agents such as mannitol, or otherwise prepared for storage prior to use.

It will be understood that therapeutic agents may be placed in the organic phase or aqueous phase according to their solubility.

Nanoparticles described herein may include any other suitable components, such as phospholipids or cholesterol components, generally know or understood in the art as being suitable for inclusion in nanoparticles. Copending patent application, PCT/US2012/053307, describes a number of additional components that may be included in nanoparticles. Copending patent application, PCT/US2012/053307, is hereby incorporated herein by reference in its entirety to the extent that it does not conflict with the present disclosure.

Nanoparticles disclosed in PCT/US2012/053307 include targeting moieties that target the nanoparticles to apoptotic cells, such as moieties that target phosphatidylserine (PS). The targeting moieties are conjugated to a component of the nanoparticle. Such moieties include various polypeptides or zinc 2,2'-dipicolylamine ($Zn^{2+}$-DPA) coordination complexes. In embodiments, the nanoparticles described herein are free or substantially fee of apoptotic cell targeting moieties. In embodiments, the nanoparticles described herein are free or substantially fee of apoptotic cell targeting moieties that are conjugated to a component of the nanoparticle. In embodiments, the nanoparticles described herein are free or substantially fee of PS targeting moieties. In embodiments, the nanoparticles described herein are free or substantially fee of PS targeting moieties that are conjugated to a component of the nanoparticle. In embodiments, the nanoparticles described herein are free or substantially fee of PS-polypeptide targeting moieties or $Zn^{2+}$-DPA moieties. In embodiments, the nanoparticles described herein are free or substantially fee of PS-polypeptide targeting moieties or $Zn^{2+}$-DPA moieties that are conjugated to a component of the nanoparticle.

Nanoparticles disclosed in PCT/US2012/053307 include macrophage targeting moieties, such as simple sugars, conjugated to components of the nanoparticles. In embodiments, the nanoparticles described herein are free or substantially free of macrophage targeting moieties. In embodiments, the nanoparticles described herein are free or substantially free of macrophage targeting moieties that are conjugated to the nanoparticle or a component thereof. In embodiments, the nanoparticles described herein are free or substantially free of simple sugar moieties. In embodiments, the nanoparticles described herein are free or substantially free of simple sugar moieties that are conjugated to the nanoparticle or a component thereof.

VII. Use and Testing

In general, a nanoparticle as described herein may be targeted to mitochondria, specifically to the mitochondria. The nanoparticles may be used for visualization, imaging, monitoring, diagnosis, or treating diseases associated with mitochondrial dysfunction.

The performance and characteristics of nanoparticles produced herein may be tested or studied in any suitable manner. By way of example, therapeutic efficacy can be evaluated using cell-based assays. Toxicity, bio-distribution, pharmacokinetics, and efficacy studies can be tested in cells or rodents or other mammals. Zebrafish or other animal models may be employed for combined imaging and therapy studies. Rodents, rabbits, pigs, or the like may be used to evaluate diagnostic or therapeutic potential of nanoparticles. Some additional details of studies that may be performed to evaluate the performance or characteristics of the nanoparticles, which may be used for purposes of optimizing the properties of the nanoparticles are described below. However, one of skill in the art will understand that other assays and procedures may be readily performed.

Uptake and binding characteristics of nanoparticles encapsulating fluorescent QD may be evaluated in any suitable cell line, such as RAW 264.7, J774, jurkat, and HUVECs cells. The immunomodulatory role of nanoparticles may be assayed by determining the release of cytokines when these cells are exposed to varying concentrations of nanoparticles. Complement activation may be studied to identify which pathways are triggered using columns to isolate opsonized nanoparticles; e.g. as described in Salvador-Morales C, Zhang L, Langer R, Farokhzad O C, Immunocompatibility properties of lipid-polymer hybrid nanoparticles with heterogeneous surface functional groups, *Biomaterials* 30: 2231-2240, (2009). Fluorescence measurements may be carried out using a plate reader, FACS, or the like. Because nanoparticle size is an important factor that determines biodistribution, Nanoparticles may be binned into various sizes (e.g., 20-40, 40-60, 60-80, 80-100, 100-150, and 150-300 nm) and tested according to size:

Any cell type appropriate for a therapeutic agent employed in a nanoparticle may be used to evaluate therapeutic efficacy or proper targeting. Assays appropriate for the therapeutic or pharmacologic outcome may be employed, as are generally understood or known in the art.

Biodistribution (bioD) and pharmacokinetic (PK) studies may be carried out in rats or other suitable mammals. For PK and bioD analysis, Sprague Dawley rats may be dosed with QD-labeled, apoptosis-targeting, macrophage-targeting nanoparticles or similar nanoparticles without the targeting groups, through a lateral tail vein injection. The bioD may be followed initially by fluorescence imaging for 1-24 h after injection. Animals may be sacrificed; and brain, heart, intestine, liver, spleen, kidney, muscle, bone, lung, lymph nodes, gut, and skin may be excised, weighed, homogenized, and Cd from QD may be quantified using ICP-MS. Tissue concentration may be expressed as % of injected dose per gram of tissue (% ID/g). Blood half-life may be calculated from blood Cd concentrations at various time points Therapeutic dosages of nanoparticles effective for human use can be estimated from animal studies according to well-known techniques, such as surface area or weight based scaling.

In the following, non-limiting examples are presented, which describe various embodiments of representative nanoparticles, methods for producing the nanoparticles, and methods for using the nanoparticles.

EXAMPLES

Methods

A. Synthesis of PLGA-b-PEG-TPP

Synthesis of PLGA-b-PEG-TPP. HO-PEG-OH (0.75 g; 0.23 mmol), PLGA-COOH (0.50 g; 0.1 mmol), and 4-dimethylaminopyridine (0.01 g; 0.08 mmol) were dissolved in 7 mL of dry $CH_2Cl_2$. A 2-mL $CH_2Cl_2$ solution of N,N'-dicyclohexycarbodiimide (DCC) (0.02 g; 0.1 mmol) was added dropwise to the reaction mixture at 0° C. with stirring. The mixture was warmed to room temperature and stirred overnight. Insoluble dicyclohexylurea was filtered, and the mixture was precipitated from 50 mL of 50:50 diethyl ether and methanol. The resulting solid was centrifuged at 1,400×g for 15 min at 4° C. As a final purification, a methanolic solution of PLGA-b-PEG-OH was precipitated repeatedly, washed with cold diethyl ether, and isolated as a white solid in a 30% (0.2 g) yield. $^1$H-NMR ($CHCl_3$-d): δ 5.3 [m, ($OCHCH_3C(O)$)], 4.9 [m, ($OCH_2C(O)$)], 3.6 [s, ($OCH_2$)], 1.9 [m, ($CH_3CH$)]. $_{13}$C-NMR ($CHCl_3$-d): δ 169.6, 166.5, 66.0, 61.1, 60.9, 16.89, 15.46. Gel permeation chromatography: $M_a$=6,900 g/mol, $M_w$=9,200 g/mol, $M_z$=12,300 g/mol, PDI=1.33. PLGA-b-PEG-OH (0.29 g; 0.03 mmol). (5-carboxypentyl)triphenylphosphonium cation (31) (0.11 g; 0.29 mmol), and 4-dimethylaminopyridine (0.007 g; 0.06 mmol) were dissolved in 3 mL of dry CECIL DCC (0.06 g; 0.29 mmol) was dissolved in $CH_2Cl_2$ (1 mL) and added dropwise to the reaction mixture at 0° C. with stirring. The mixture was stirred overnight at room temperature, after which any dicyclohexylurea formed was filtered off. Then 50 mL of cold diethyl ether was added to the resulting mixture to precipitate the polymer. The solid was centrifuged at 1,400×g for 15 min at 4° C. The solvent was removed, and the solid was lyophilized. The polymer was isolated as a white solid in 99% (0.3 g) yield. $_1$H-NMR ($CHCl_3$-d): δ 7.9-7.6 [m, 15H (Ar)], 5.3 [m, ($OCHCH_3C(O)$)], 4.9 [m, ($OCH_2C(O)$)], 3.6 [s, ($OCH_2$)], 1.9 [m, ($CH3CH$)]. $^{13}$C-NMR (CHCl3-d): δ 166.5, 135.3, 133.9, 130.7, 66.0, 61.0, 16.89, 15.46. IR: ν cm−1 3,029 (C—H sp2), 2,944 (C—H sp3), 2,200-2,000 (C—H Ar), 1,741 (C═O). $^{31}$P-NMR (CHCl3-d): δ 24.37.

B. Synthesis of PLGA-b-PEG-OD

PLGA-COOH (0.4 g; 80 µmol), 1-ethyl-3-(3-dimethylaminopropyl) carbodiimide (EDC) (12.4 mg; 80 µmol), and NHS (9 mg; 80 µmol) were dissolved in 3 mL of dimethylformamide (DMF), and a 250-µL solution of 8 µM QD-PEG-NH2 was added. The mixture was stirred at room temperature for 24 h, then filtered through a 100-kDa cutoff Amicon filter (Millipore). The resulting solid was dissolved in H2O, lyophilized overnight, and then resuspended in DMF. PLGA-b-PEG-QDs were characterized using dynamic light scattering (DLS), which gave a hydrodynamic diameter of 10.1±0.1 nm and a PDI of 0.3.

C. Synthesis of Targeted and Nontargeted Nanoparticles

Nanoparticles were synthesized by the nanoprecipitation method as generally described in Marrache and Dhar (2012), Proc. Natl. Acad. Sci. USA 109: 16288-16293, Kolishetti et al. (2010) *Proc. Natl. Acad. Sci. USA* 107:17939-17944; and Dhar et al. (201.1) *Proc. Natl. Acad. Sci. USA* 108:1.850-1855. Briefly, PLGA-b-PEG-OH or PLGA-b-PEG-TPP in acetonitrile to a final polymer concentration of 5 mg/mL was added dropwise to nanopure water with constant stirring. The nanoparticles were then stirred for 2 h. Organic solvent was removed by three washes and filtering through a 100-kDa cutoff Amicon filter (Millipore). The nanoparticles were resuspended in nanopure water and stored at 4° C. until further use. DLS measurements were performed to determine nanoparticle size, PDI, and zeta potential. PLGA-b-PEG-TPP nanoparticles with tunable sizes were synthesized by blending predefined ratios of PLGA-COOH (0, 10%, 20%, 35%, 50%, 70%, and 90%) with PLGA-b-PEG-TPP following the nanoprecipitation method. Surface charges of PLGA-b-PEG-TPP nanoparticles were varied by blending predefined ratios of PLGA-b-PEG-TPP (0, 15%, 35%, 50%, 65%, 80%, 90%, and 100%) with PLGA-b-PEG-OH following the aforementioned nanoprecipitation method. QD-blended nanoparticles were synthesized Mowing this nanoprecipitation method using PLGA-b-PEG-OH or PLGA-b-PEG-TPP in DMF:acetonitrile (1:9 ratio) with PLGA-b-PEG-QD (10 mmol solution in DMF) to a final polymer concentration of 5 mg/mL. DLS measurements were performed to determine size, PDI, and zeta potential. All nanoparticles were characterized using TEM. For the synthesis of therapeutics-loaded nanoparticles, PLGA-b-PEG-OH or PLGA-b-PEG-TPP (50 mg/mL in DMF) was mixed with a predefined amount of therapeutics (10 mg/mL in DMF) and diluted with acetonitrile to a final polymer concentration of 5 mg/mL. This mixture was added dropwise to nanopure water with constant stirring following the nanoprecipitation method. DLS measurements were performed to determine size, PDI, and zeta potential. Drug loading and encapsulation efficiency were determined by dissolving the polymeric core and using HPLC to quantify the amount of the therapeutics in the nanoparticles.

D. Quantification of Nanoparticles in the Intracellular Compartments

QD-blended nanoparticles (10 μM) of varying sizes and zeta potentials were internalized in HeLa cells ($1.5 \times 10^7$ cells) for 12 h. After internalization, the mitochondria and the cytosol were isolated using a mitochondria isolation kit for mammalian cells. The cytosolic and mitochondrial fractions were then analyzed for Cd concentration in the QD by ICP-MS. A bicinchoninic acid (BCA) assay was performed on the isolated mitochondrial and cytosolic fractions to calculate the amount of Cd per microgram of protein isolated.

E. Adipogenesis Assay

To induce adipogenesis, 3T3-L1 preadipocytes were plated on a 96-well plate at a density of 5,000 cells per well and grown to confluence. The antiadipogenesis properties of targeted and nontargeted nanoparticles loaded with 2,4-DNP and free 2,4-DNP were evaluated by internalizing the nanoparticles on day 1 of the adipogenesis assay. Also on day 1, cells were induced to differentiate in a differentiation DMEM media containing 10% FBS supplemented with 0.5 mmol 3-isobutyl-1-methylxanthine (IBMX), 0.5 μM dexamethasone, and 20 nM insulin. On day 3, the induction medium was replaced with insulin medium containing DMEM, 10% FBS, and 20 nM. insulin. After 6 d of treatment, cells were analyzed for triglyceride accumulation using the AdipoRed (Lonza) assay following the manufacturer's instructions.

F. Biodistribution and Pharmacokinetic Analysis

Sprague Dawley rats were administered PLGA-b-PEG-TPP-QD nanoparticles intravenously. Variation of Cd levels in plasma with time, organ distribution, and excretion properties were determined. Control rats were injected with saline.

G. Statistics

All data are expressed as mean±SD. Differences among targeted, nontargeted, and free drugs were assessed by one-way ANOVA. $P<0.05$ was considered to indicate statistical significance.

Results and Discussion

A. Development of Targeted Blended Nanoparticles

Figure 2:
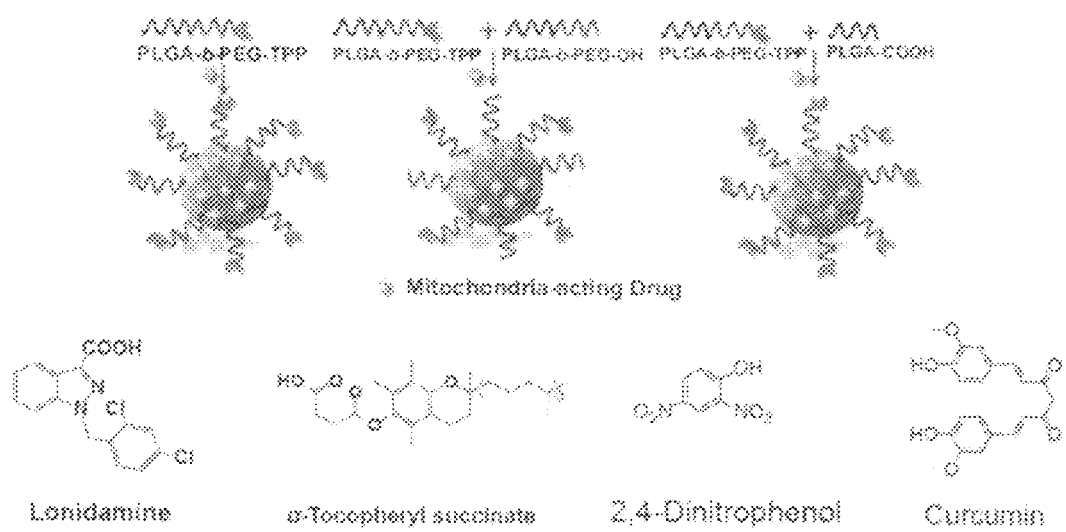
FIG. 2 is a schematic drawing illustrating construction of targeted and nontargeted nanoparticles by blending PLGA-b-PEG-OH and PLGA-COOH with PLGA-b-PEG-TPP, with mitochondria-acting therapeutics used as payloads.

Advances in understanding the importance of size, shape, and surface charge of PLGA-based nanoparticles for mitochondrial uptake have the potential of creating opportunities for the development of targeted delivery vehicles for mitochondrial dysfunction-related diseases. We blended a mitochondrial-targeting functionalized polymer, PLGA-b-PEG-TPP, with PLGA-COOH or with PLGA-b-PEG-OH to vary the size and surface charge of the resultant nanoparticles, to study the effect of these properties on the mitochondrial uptake and determine an optimal formulation. The likelihood of variation in nanoparticle properties increases with the number of processing steps required for synthesis. We anticipated that incorporating the TPP targeting moiety in the polymer before nanoparticle synthesis would minimize such variability. To deliver therapeutics inside the mitochondria with high efficiency, we synthesized a biodegradable polymer with a terminal OH group (PLGA-b-PEG-OH) to enable the conjugation of TPP to obtain PLGA-b-PEG-TPP (FIG. 1). The conjugation of the targeting ligand affected the key properties of the nanoparticles, including zeta potential, size, cellular uptake, and intracellular trafficking. We synthesized the blended nanoparticles using a nanoprecipitation method as described above (FIG. 2), and obtained targeted and nontargeted blended nanoparticles with reproducible diameter and surface charges in more than three independent nanoprecipitation experiments.

B. Tuning of Size and Charge for Mitochondrial Uptake

Figure 3:
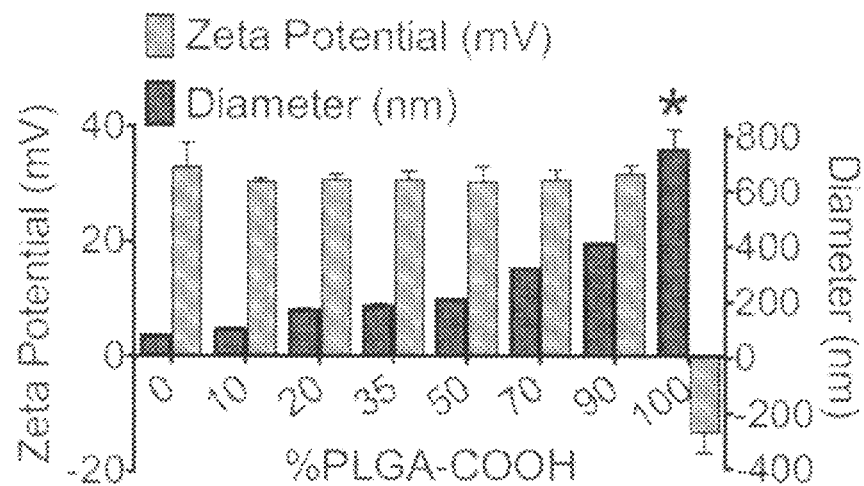
FIG. 3 is a bar graph showing size and zeta potential variation in blended nanoparticles from PLGA-b-PEG-TPP and PLGA-COOH. *Nanoparticles from 100% PLGA-COOH are unstable, and nanoparticle diameter varies from 700 nm to 10 μm depending on the batch preparation.
Figure 4:
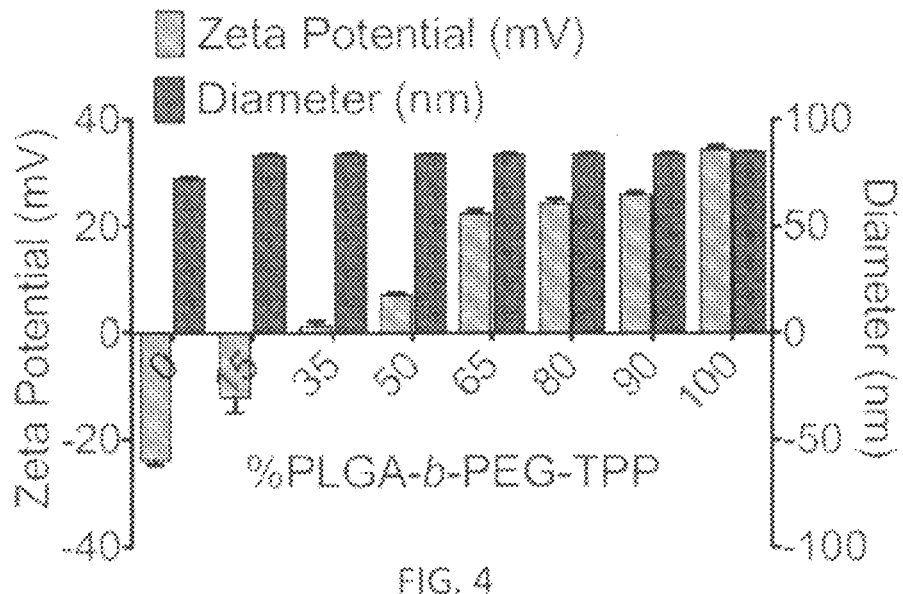
FIG. 4 is a bar graph showing size and zeta potential variation in nanoparticles by blending PLGA-b-PEG-TPP with PLGA-b-PEG-OH.
Figure 5A:
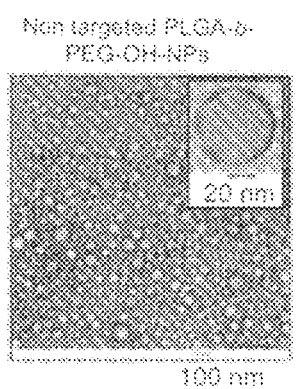
FIGS. 5A-F are TEM images of targeted and nontargeted blended nanoparticles. All of the TEM samples except the QD-blended nanoparticles were stained with sterile 2% (wt/vol) uranyl acetate aqueous solution for 15 min before imaging.
Figure 5B:
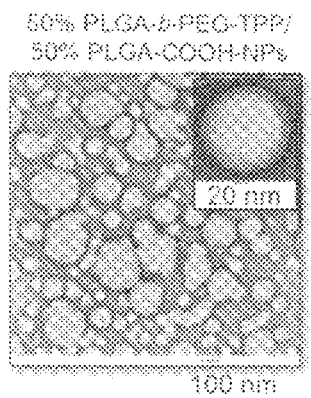
Figure 5C:
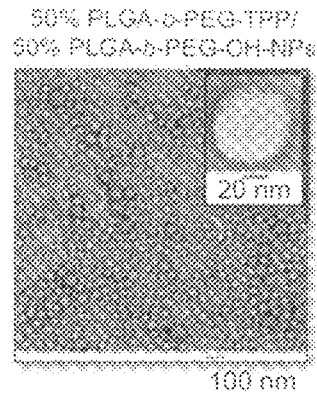
Figure 5D:
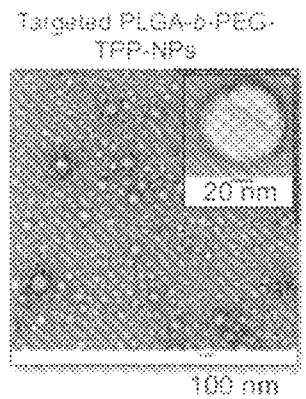
Figure 5E:
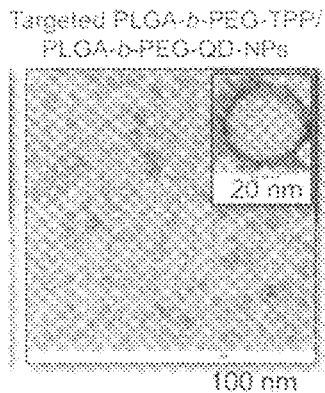
Figure 5F:
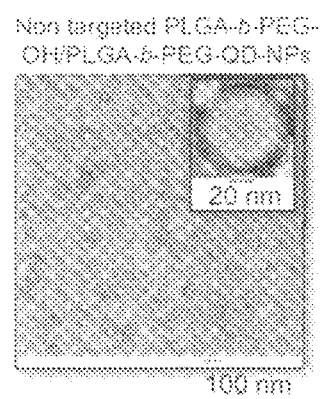

We undertook a representative and comprehensive study to address the effect of size and surface charge on the mitochondrial uptake. We felt that it was important to fabricate nanoparticles of different sizes and surface. charges but with all other properties identical or substantially identical. We blended varying amounts of PLGA-COOH with PLGA-b-PEG-TPP to construct a library of nanoparticles with varying size and constant surface charges. Using the blending technology, we were able to tune nanoparticles sizes from ~80 to ~410 nm (FIG. 3) while keeping the number of TPP moiety constant, as evidenced by the constant surface charge (FIG. 3). To explore the effect of surface charge on the mitochondrial uptake, we blended predefined amounts of PLGA-b-PEG-OH with PLGA-b-PEG-TPP. The surface charge was successfully altered without changing the main scaffold and nanoparticle size (FIG. 4). These nanoparticle libraries exhibited homogenous populations of similar shape (TEM images; FIGS. 5A-F), allowing us to explore the effects of nanoparticle size and charge on mitochondrial uptake.

C. Mitochondria-Targeting Properties

Figure 7A:
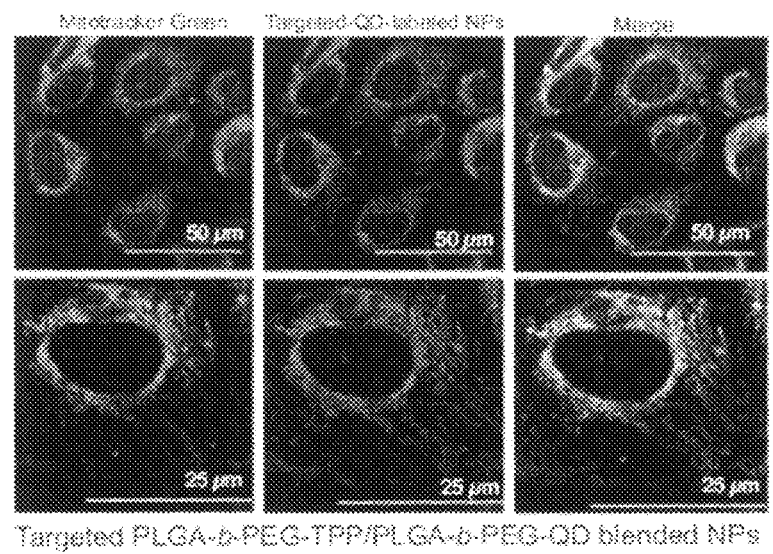
FIGS. 7A-B are images of cells showing subcellular localization of red fluorescent-targeted PLGA-b-PEG-TPP/PLGA-b-PEG-QD (A) and nontargeted PLGA-b-PEG-OH/PLGA-b-PEG-QD (B) blended nanoparticles. HeLa cells were exposed to targeted nanoparticles (diameter, 79 nm; zeta potential; 27.4 mV) and nontargeted nanoparticles (diameter, 79 nm; zeta potential, −26.5 mV) at 10 μM for 4 h. The cells were then stained with the mitochondria marker MitoTracker Green (Invitrogen), fixed, and observed by wide-field fluorescence microscopy. The merged images and higher-magnification images show effective overlap of mitochondrial staining (green) and targeted nanoparticles (red). No significant overlap was observed with nontargeted nanoparticles.
Figure 7B:
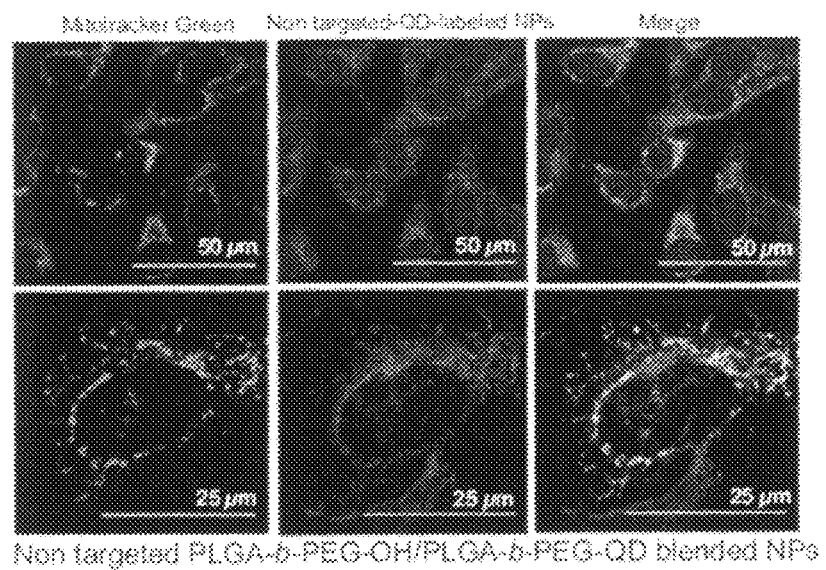

The cellular uptake profile of a nanoparticle system reflects the system's efficiency and bioavailability. Along with a quantitative evaluation of cellular uptake, subcellular location is important for assessing the effectiveness of the current nanoparticle platform. We used a robust fluorescent reporter quantum dot (QD) to investigate the distribution of the targeted and nontargeted nanoparticles in human cervical cancer HeLa cells. We used a QD-conjugated amine-terminated PEG, $NH_2$-PEG-QD, to track the nanoparticles in the intracellular compartments. PLGA-COOH was conjugated to $NH_2$-PEG-QD to yield a triblock copolymer, PLGA-b-PEG-QD (FIG. 1). We monitored the internalization of the targeted and nontargeted nanoparticles by blending PLGA-b-PEG-QD with PLGA-b-PEG-TPP and with PLGA-b-PEG-OH, respectively. Confocal microscopy analysis of the treated cells indicated significantly greater uptake of targeted nanoparticles than of nontargeted nanoparticles in the mitochondria of cells (FIGS. 7A-B). A comparison of fluorescence intensities indicated a significantly greater overall uptake of the positively charged targeted nanoparticles compared with nontargeted nanoparticles. Quantitative analysis using the ImageJ "colocalization finder" plug-in revealed significant colocalization of the targeted nanoparticles with MitoTracker Green (Invitrogen) in the mitochondria of cells (Pearson's correlation coefficient, $\rho=0.53$).

With the nontargeted nanoparticles, the red signals of the nanoparticles and the mitochondrial staining differed in position, as demonstrated by a lower ρ value (ρ=0.03).

D. Endosomal and Lysosomal Escape Properties

The uptake and intracellular trafficking of nanoparticles occurs along several competing pathways. The use of nanoparticles to target mitochondria is often limited by the fact that the nanoparticles are taken up by the endosomal pathway, and that endosomes serve as a barrier to mitochondrial trafficking. We performed a time-dependent uptake study using the early endosome marker EAA-1 to investigate the fusogenic character necessary for efficient endosomal escape of the targeted nanoparticles. For the targeted nanoparticles, colocalization with endosomes was observed in the first hour and was decreased by 2 h. Over time, the targeted nanoparticles exhibited complete endosomal escape and localized in the mitochondria of cells (FIGS. 7A-B); however, significant colocalization with the early endosomes was observed with the nontargeted nanoparticles even after 4 h. The highly efficient endosomal escape of the targeted nanoparticles may be attributed to these nanoparticles high buffering capacity, which may cause them to act as "proton sponges." Proton absorbance by buffering of positively charged PEG should prevent acidification of endosomal vesicles, thereby increasing the ATPase-mediated influx of protons and counter ions, which in turn may lead to osmotic swelling, endosomal membrane rupture, and eventual leakage of the nanoparticles into the cytosol, making them accessible for mitochondrial uptake.

Figure 8A:
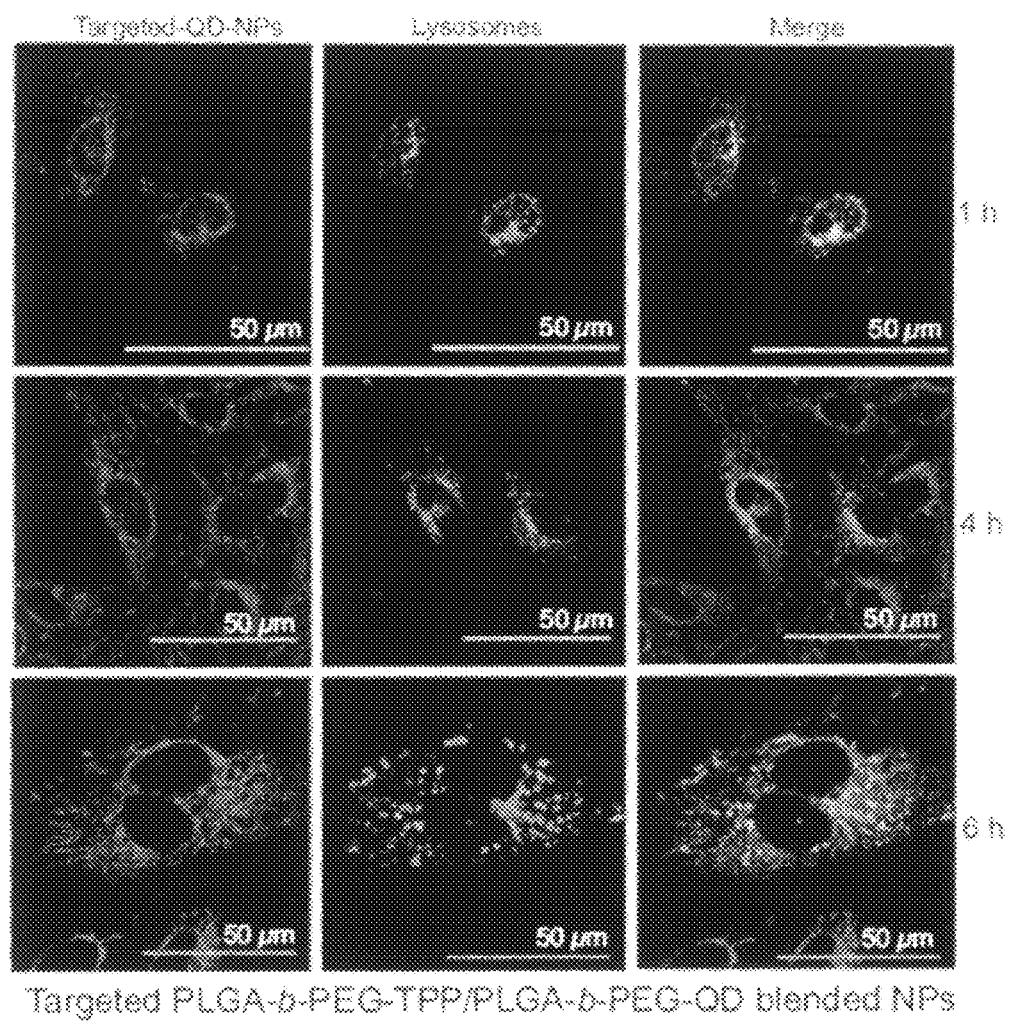
FIGS. 8A-B are con focal images of time-dependent uptake of targeted PLGA-b-PEG-TPP/PLGA-b-PEGQD blended nanoparticles (A) and nontargeted PLGA-b-PEG-OH/PLGA-b-PEG-QD blended nanoparticles (B) in HeLa cells. Lysosomes were stained with CellLight lysosomes-GFP, BacMam 2.0 (Life Technologies) (green).
Figure 8B:
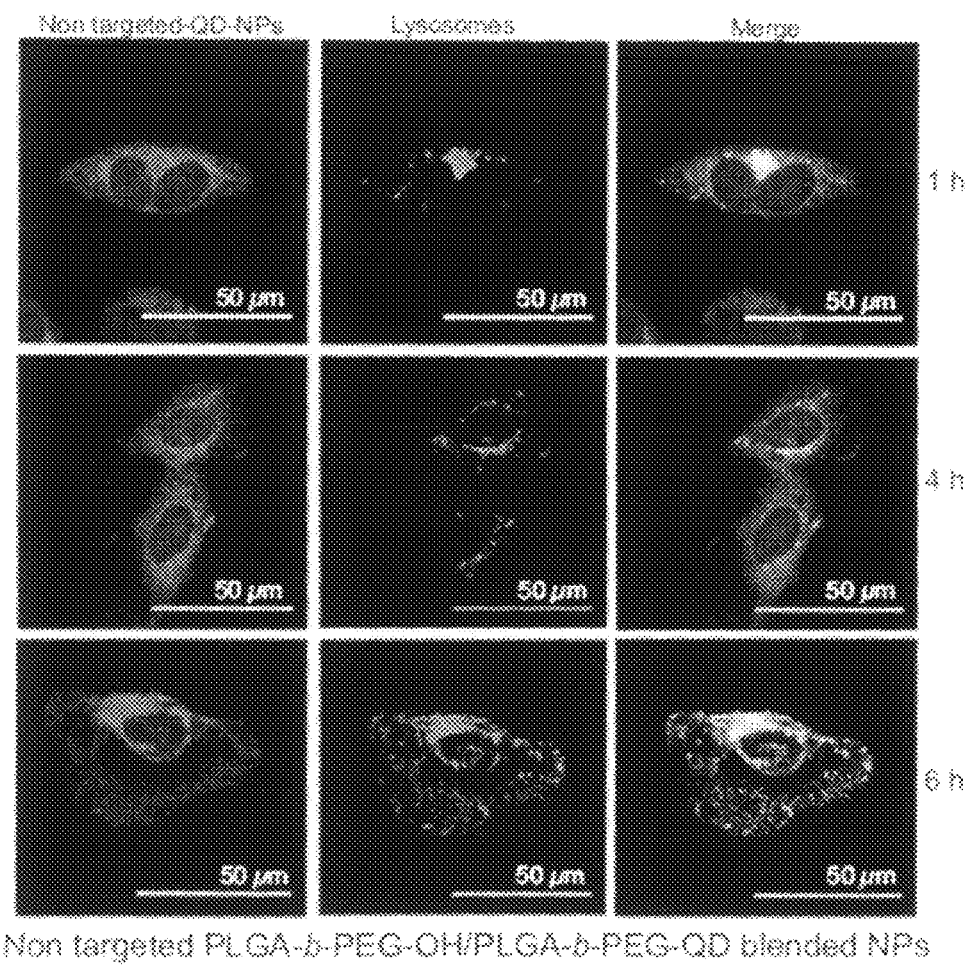

To further support the findings that our nanoparticles have high endosomal escapability and that some of the targeted nanoparticles are not engaged in trafficking to lysosomes, we studied a time-dependent colocalization of the nanoparticles with lysosomes (FIGS. 8A-B). For the targeted nanoparticles, colocalization with lysosomes decreased over time, suggesting lysosomal escape ability, whereas the nontargeted nanoparticles were distributed in both the lysosomes and the cytoplasm.

E. Stability and Immunologic Effect of Nanoparticles

Various positively charged nanoparticles demonstrate interactions with serum proteins, causing aggregation owing to the surface adsorption of negatively charged proteins. Serum proteins had no effect on the size and polydispersity index (PDI) of our targeted nanoparticles on incubation with 10% (vol/vol) FBS in DMEM: or 10% (vol/vol) FBS in $H_2O$ for 7 d. This finding was further supported by the observation that zeta potentials of the targeted nanoparticles changed only minimally after contact with 10% FBS in DMEM or $H_2O$ for 7 d, with no visible aggregation of particles. These findings suggest that the excellent stability of the targeted nanoparticles in serum makes them suitable for in vivo application.

Figure 6A:
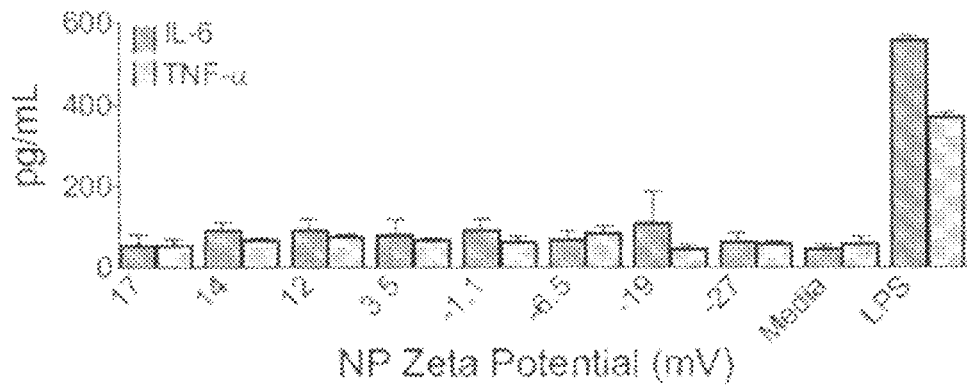
FIGS. 6A-B are bar graphs showing secretion of IL-6 and TNF-α in the media with charge-varied (A) and, size-varied (A) nanoparticles (0.5 mg/nit) after 12 h in RAW 264.7 macrophages.
Figure 6B:
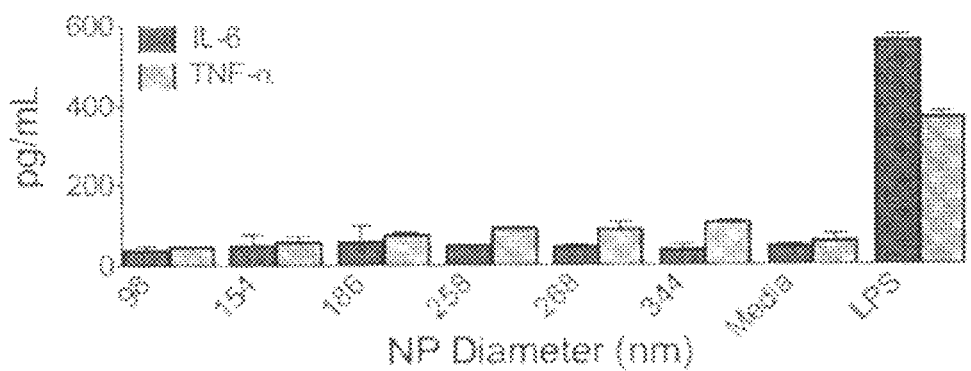

This engineered nanoparticle platform can be used to transport therapeutics for in vivo application if they do not trigger an immune response. Immune cells in the bloodstream and in tissues have a propensity to engulf and eliminate positively charged nanoparticles: We evaluated immune responses from size- and charge-varied nanoparticles in terms of the production of proinflammatory cytokines IL-6 and TNF-α in RAW 264.7 macrophages by ELISA, with LPS used as a control. The charge-varying nanoparticles did not exhibit a pronounced immune response; however, nanoparticles of >200 nm diameter demonstrated TNF-α production (FIGS. 6A-B). These findings confirm that nanoparticles of suitable size and charge are nonimmunogenic and can be used in systemic in vivo studies.

F. Quantification of Targeted Nanoparticles in Subcellular Compartments

Figure 9:
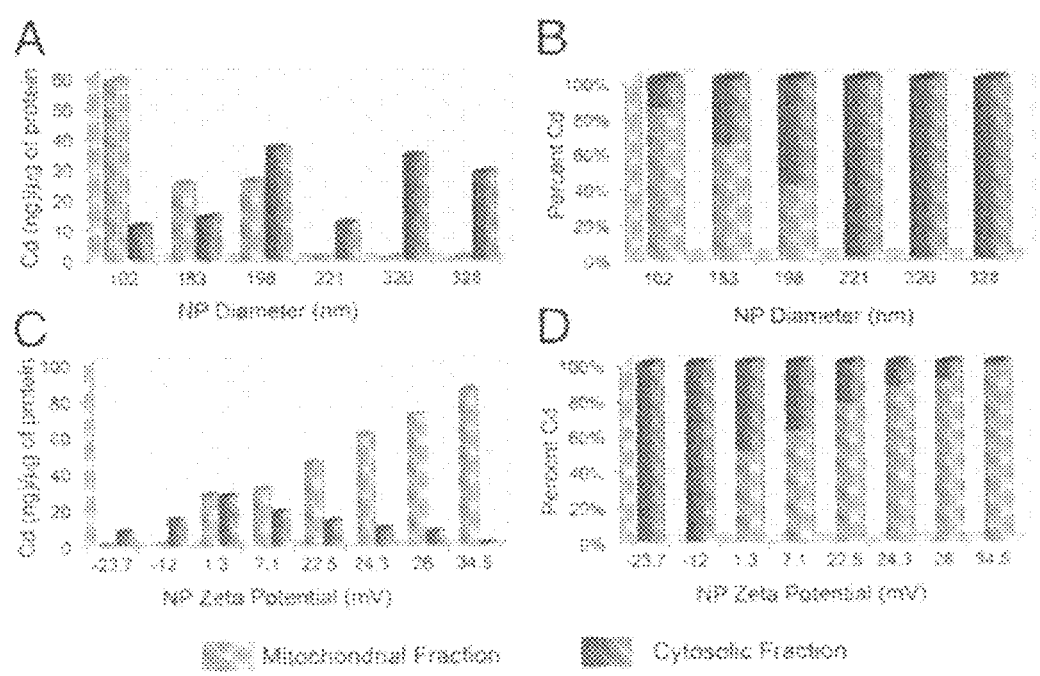
FIGS. 9A-D are bar graphs showing mitochondrial and cytosolic distribution of targeted PLGA-b-PEGTPP/PLGA-h-PEG-QD blended nanoparticles in HeLa cells by ICP-MS analysis. (A) Effect of size on uptake of nanoparticles. (B) Overall cellular uptake of size-varying nanoparticles. (C) Effect of zeta potential on cellular trafficking of nanoparticles. (D) Overall cellular uptake of zeta potential-varying nanoparticles.

To cross the mitochondrial membranes, nanoparticles are transported across the outer membrane through the general import pore. We anticipated that the complicated structures of the tubular, vesicular, and flat cristae and their slight connections to the inner mitochondrial membrane might impose constraints on nanoparticle mobility and make their diffusion a very complicated, size-dependent process. The inner membrane potential ($\Delta\Psi m$), which is negative on the inside, plays a major function in import by exerting an electrophoretic effect on the positively charged species. Nanoparticles with a high positive charge are expected to be imported at a lower $\Delta\Psi m$ than nanoparticles with a lower positive charge; thus, using a HeLa model cell line, we performed a comparative evaluation of the effect. of nanoparticles size and charge in crossing the mitochondrial inner membrane (FIGS. 9A-D). We treated HeLa cells with targeted PLGA-b-PEG-TPP/PLGA-b-PEG-QD blended nanoparticles of different sizes but similar zeta potential, then performed a quantitative investigation using inductively coupled plasma mass spectrometry (ICP-MS) to estimate the amount of cadmium (Cd) from the QDs internalized by the cells. Evaluation of the mitochondrial uptake of nanoparticles of 80-330 nm diameter showed a trend toward a maximum uptake of 80- to 100-nm-diameter particles. Histograms showing the number of nanoparticles in the cytosolic and mitochondrial fractions versus nanoparticles size indicate that the cellular uptake of nanoparticles is heavily dependent on particle size (FIG. 9A-B). We studied the effect of nanoparticle surface charge on cellular and mitochondrial uptake using a library of nanoparticles with varying surface charges but similar hydrodynamic diameters, and detected no mitochondrial uptake (FIG. 9C) and very little overall cellular uptake (FIG. 9D) of negatively charged nanoparticles. Cellular uptake increased as the surface charge reached 1.3 mV and remained constant up to a surface charge of ~22 mV, with increased mitochondrial uptake. We found another jump in cellular uptake as the surface charge increased to ~34 mV and reached saturation. Mitochondrial uptake increased significantly with the more positively charged nanoparticles. This systematic investigation of the effect of nanoparticle diameter and surface charge may be useful in the design of optimized nanoparticle platforms for mitochondrial trafficking.

G. Delivery of Therapeutics to Dysfunctional Mitochondria

As a proof of concept demonstration of versatility of this system, we studied the delivery of mitochondria-acting therapeutics for the management of neurodegeneration, obesity, and cancer. We synthesized targeted and nontargeted nanoparticles loaded with therapeutics with high loading and encapsulation efficiency using the nanoprecipitation method.

H. Application in Neurodegenerative Disease

Figure 10:
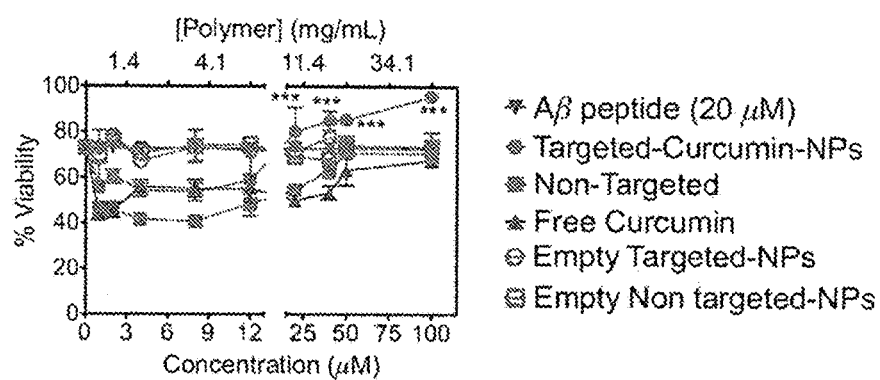
FIG. 10 is a bar graph showing the effect on percent survival of IMR-32 neuroblastoma cells after treatment with targeted curcumin nanoparticles, nontargeted curcumin nanoparticles, and free curcumin against Aβ-induced cytotoxicity. The asterisk represents significant differences between targeted curcumin nanoparticles, nontargeted curcumin nanoparticles, and free curcumin according to one-way ANOVA with Tukey's post hoc test; P<0.001.

Amyloid-like plaques define the neuropathology of AD. Aggregations of the beta amyloid (Aβ) peptide form amyloid-like lesions, and thus reduction of amyloid burden by preventing Aβ formation represents an attractive approach to improving the therapeutic arsenal for AD. Curcumin is known to inhibit Aβ and the associated mitochondrial oxidative stress; however, its low bioavailability and photodegradation are major concerns. With such issues in mind, we formulated targeted curcumin-loaded nanoparticles to provide photostability and enhance mitochondrial uptake. An in vitro survival evaluation of human neuroblastoma IMR-32 cells treated with 20 μMAβ using the MTT [3-(4,5-dimethylthiazole-2-yl)-2,5-diphenyltetrazolium bromide] assay demonstrated enhanced neuroprotection with the targeted curcumin nanoparticles compared with the nontargeted curcumin nanoparticles or free curcumin (FIG. 10) against Aβ, which accounts for the targeted delivery of curcumin to the mitochondria of cells.

I. Application in Cancer Chemotherapy

Figures 11A, 11B, 11C:
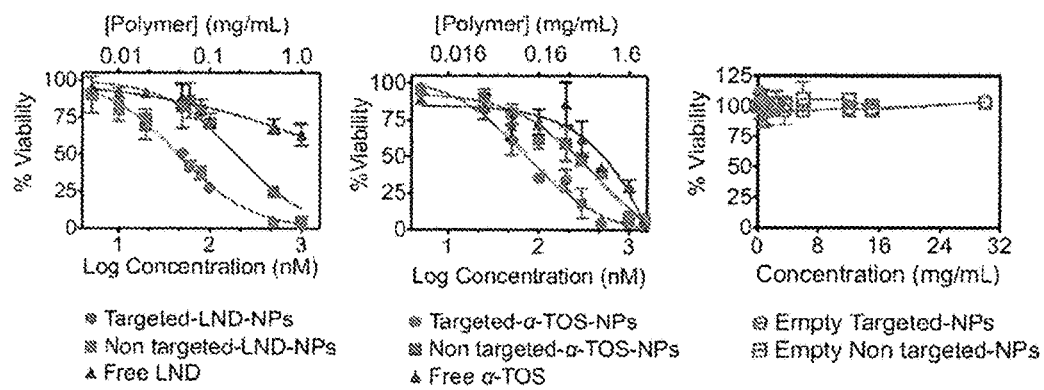
FIGS. 11A-C are bar graphs showing cytotoxicity profiles of targeted LND nanoparticles, nontargeted LND nanoparticles, free LND (A); targeted α-TOS nanoparticles, nontargeted α-TOS nanoparticles, free α-TOS in HeLa cells (B); and empty targeted nanoparticles, and empty nontargeted nanoparticles in HeLa cells (C).

Mitochondria have emerged as a specific target for cancer treatment. Mitochondria-acting LND and α-TOS were selected to demonstrate the applicability of our system in cancer. The selectivity and efficiency of LND and α-TOS against cancer cells depend on their ability to target the mitochondria of cells. To evaluate the efficacy of our targeted nanoparticles in delivering LND and α-TOS, we performed MIT assays in HeLa cells. The IC50 value for targeted LND nanoparticles was ~5-fold lower than that for nontargeted nanoparticles and 108-fold lower than that for free-form (FIG. 11A), indicating a greater cytotoxic effect. A greater cytotoxic effect also was observed with targeted α-TOS nanoparticles compared with nontargeted α-TOS nanoparticles and free α-TOS (1050 75±2 nM, 230±4 nM, and 381±5 nM, respectively) (FIG. 11B). Preferential localization in the target organelle accounts for the enhanced cytotoxicity of both LND and α-TOS encapsulated in the targeted nanoparticles. Our finding of no cytotoxic effect of the empty PLGA-b-PEG-TPP nanoparticles even at high concentrations rules out a contribution of the delivery system or high zeta potentials to any cellular toxicity (FIG. 11C).

J. Possible Application in Obesity

Obesity has become a global health problem owing to its association with various metabolic disorders, including type 2 diabetes, cardiovascular diseases, and certain types of cancer. Because of the limited efficacy and undesirable side effects associated with the currently available antiobesity medications, attention has been focused on developing delivery vehicles that can directly deliver drugs to subcellular sites to modulate energy metabolism. The notable success of the mitochondrial uncoupler 2,4-DNP as a treatment for human obesity demonstrates that the beneficial effect of uncoupling on energy expenditure is not overwhelmed by compensatory increases in caloric intake. However, 2,4-DNP's narrow therapeutic window led to the abandonment of its use. A recent study found that 2,4-DNP linked to TPP in a covalent manner is ineffective at uncoupling. Concerns about the narrow therapeutic window and failure of the covalently linked uncoupler have led to the evaluation of mitochondria-targeted nanoparticles in directing this uncoupler to the mitochondria of cells. To examine whether encapsulation of 2,4-DNP in targeted nanoparticles can suppress the induced differentiation of 3T3-L1 preadipocytes at a low dosage that is insufficient to exert cytotoxicity, we continuously exposed 3T3-L1 cells to 1 µM, 4 µM, 25 µM, and 100 µM targeted 2,4-DNP nanoparticles (FIGS. 12A-D and 13) during the differentiation period for 7 d, and evaluated cell viability and intracellular lipid accumulation. Nontargeted 2,4-DNP nanoparticles and free 2,4-DNP were used as controls. The presence of 1 µM, 4 µM, or 100 µM targeted 2,4-DNP nanoparticles for 7 d during the differentiation period did not influence cell viability, but did produce a significant reduction in lipid accumulation compared with the nontargeted 2,4-DNP nanoparticles or free 2,4-DNP (FIGS. 12A-D and 13). Free 2,4-DNP at a concentration of 100 µM demonstrated cellular toxicity. These results indicate that 2,4-DNP in the targeted nanoparticles can suppress the adipocytic differentiation of 3T3-L1 cells at a low concentration (1 or 4 µM) and do not exert a cytotoxic effect on these cells. We demonstrated that 2,4-DNP can be delivered to the mitochondria of cells using a targeted polymeric nanoparticle system to reduce lipid accumulation at a lower dose compared with the free form for possible application in the management of obesity.

K. Biodistribution and Pharmacokinetics

Figure 14:
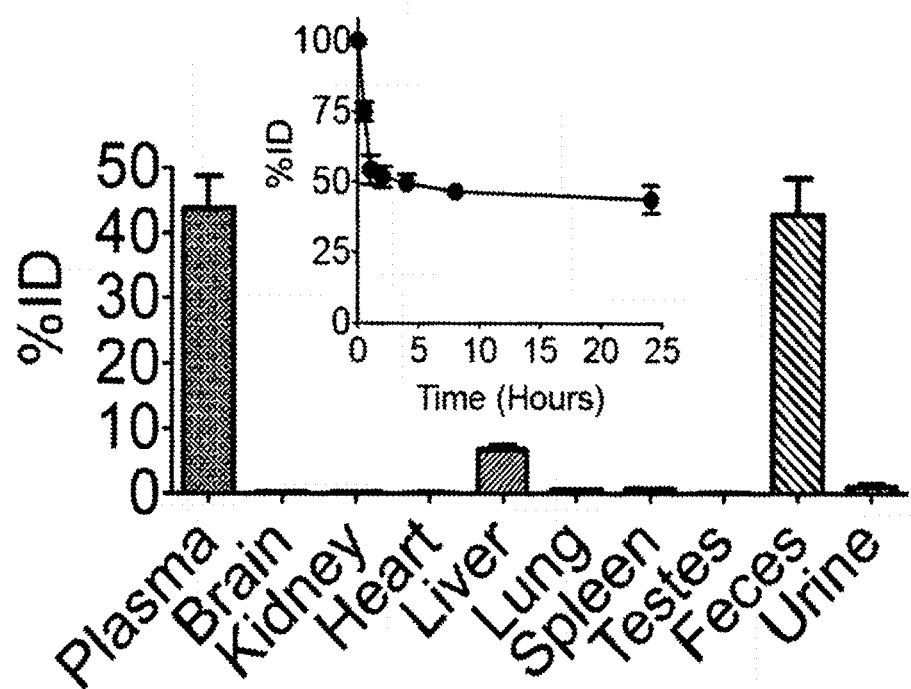
FIG. 14 is a graph showing in vivo biodistribution and pharmacokinetics of targeted nanoparticles in rats.

Biodistribution and pharmacokinetic and excretion of targeted PLGA-b-PEG-TPP-QD nanoparticles (NPs) in male Sprague Dawley rats following intravenous administration were evaluated. The variation of Cd levels in plasma with time, organ distribution, and excretion properties are shown in FIG. 14. Prolonged NP residence in plasma of these targeted NPs was observed. Among the organs studied, maximum Cd was observed in the liver. These highly positively charged NPs demonstrate rapid hepatobiliary excretion. These NPs, presumably due to the high positive charge, are quickly excreted from the liver into the gastrointestinal tract in comparison with negatively charged PLGA-b-PEG-COOH-NPs, which usually remain sequestered within the liver.

FIG. 15 is a table presenting more detailed information regarding the pharmacokinetic data.

CONCLUSION

In this proof-of-concept study, we have demonstrated that a suitably engineered mitochondria-targeted biodegradable PLGA-based nanoparticle delivery system can be made to enter the mitochondria of cells with high efficacy by fine-tuning nanoparticle surface charge and size. Not all types of nanoparticles have the ability to enter mitochondria, because they cannot cross the complex double membrane owing to restrictions in programming surface charge and size. No previous report has examined the relationship between nanoparticle size and charge for efficient import to the mitochondria. This rationalized study addressing the effects of surface charge and diameter on the intracellular trafficking of PLGA-based nanoparticles provides a generalized approach to the design of biodegradable nanocarriers for application in mitochondrial delivery. These targeted nanoparticles can be used in various mitochondrial dysfunction-related disorders, including AD, obesity, and cancer. This work highlights several exceptionally promising research directions and provides a platform for diverse applications of PLGA-based nanoparticles that can be integrated for imaging Thus, embodiments of NANOPARTICLES FOR MITOCHONDIRAL TRAFFICING OF AGENTS are disclosed. One skilled in the art will appreciate that the nanoparticles and methods described herein can be practiced with embodiments other than those disclosed. The disclosed embodiments are presented for purposes of illustration and not limitation.

What is claimed is:

1. A nanoparticle, comprising:
   a hydrophobic nanoparticle core;
   a hydrophilic layer surrounding the core; and
   a mitochondria targeting moiety tethered to the core,
   wherein the nanoparticle has a diameter of from about 10 nanometers to about 200 nanometers or less and has a zeta potential of about 0 mV or greater.

2. A nanoparticle according to claim 1, wherein the nanoparticle has a diameter of from about 80 nanometers to about 100 nanometers.

3. A nanoparticle according to claim 1, wherein the nanoparticle has a zeta potential of about 1 mV or greater.

4. A nanoparticle according to claim 1, wherein the nanoparticle has a zeta potential of about 7 mV or greater.

5. A nanoparticle according to claim 1, wherein the nanoparticle has a zeta potential of about 20 mV or greater.

6. A nanoparticle according to claim 1, wherein the nanoparticle has a zeta potential of about 25 mV or greater.

7. A nanoparticle according to claim 1, wherein the mitochondria targeting moiety comprises a moiety selected from the group consisting of a triphenylphosphonium (TPP) moiety, a Szeto-Shiller peptide, and a rhodamine cation.

8. A nanoparticle according to claim 1, wherein the mitochondria targeting moiety comprises a triphenylphosphonium (TPP) moiety or a derivative thereof.

9. A nanoparticle according to claim 1, wherein the mitochondria targeting moiety is attached to the core via a hydrophilic polymer moiety.

10. A nanoparticle according to claim 9, wherein the hydrophilic polymer moiety comprises PEG.

11. A nanoparticle according to claim 9, wherein the hydrophilic polymer moiety is attached to a hydrophobic polymer moiety that forms at least a portion of the core.

12. A nanoparticle according to claim 1, wherein the hydrophilic layer comprises a hydrophilic polymer moiety attached to the core.

13. A nanoparticle according to claim 12, wherein the hydrophilic polymer moiety comprises polyethylene glycol (PEG).

14. A nanoparticle according to claim 12, wherein hydrophilic polymer moiety is attached to the core via a hydrophobic polymer moiety that forms at least a part of the core.

15. A nanoparticle according to claim 14, wherein the hydrophobic polymer that forms at least a part of the core is selected from a polymer comprising polylactic acid (PLA), polycaprolactone (PCL), polyglycolic acid (PGA), and polylactic-co-glycolic acid (PLGA).

16. A nanoparticle according to claim 14, wherein the hydrophobic polymer that forms at least a part of the core comprises polylactic-co-glycolic acid (PLGA).

17. A nanoparticle according to claim 1, further comprising a contrast agent.

18. A nanoparticle according to claim 17, wherein the contrast agent is selected from a quantum dot, iron oxide, and combinations thereof.

19. A nanoparticle according to claim 17, wherein the contrast agent is embedded in, or contained within, the core.

20. A nanoparticle according to claim 17, wherein the contrast agent is attached to a hydrophilic polymer moiety that is attached to the core.

21. A nanoparticle according to claim 1, wherein the nanoparticle further comprises a therapeutic agent.

22. A nanoparticle according to claim 21, wherein the therapeutic agent is selected from the group consisting of an anticancer agent, a mitochondrial uncoupling agent and an agent configured to reduce amyloid beta.

23. A nanoparticle according to claim 21, wherein the therapeutic agent is selected from the group consisting of 2,4-dinitrophenol (DNP), lonidamine (LND), α-tocopherylsuccinate (TOS), and curcumin.

24. A method for treating a patient at risk or suffering from a disease associated with mitochondrial dysfunction, comprising administering a nanoparticle according to claim 21 to the patient.

* * * * *